(12) United States Patent  (10) Patent No.: US 8,328,848 B2
Lowery et al.  (45) Date of Patent: Dec. 11, 2012

(54) INTERSPINOUS VERTEBRAL STABILIZATION DEVICES

(75) Inventors: Gary L. Lowery, Jacksonville, FL (US);
Frank T. Trautwein, Filderstadt (DE);
Guntmar H. Eisen, Tuttlingen (DE);
Marc R. Viscogliosi, New York, NY (US)

(73) Assignee: Paradigm Spine, LLC, New York, NY (US)

( * ) Notice: Subject to any disclaimer, the term of this patent is extended or adjusted under 35 U.S.C. 154(b) by 1027 days.

(21) Appl. No.: 11/535,210

(22) Filed: Sep. 26, 2006

(65) Prior Publication Data

US 2007/0161993 A1  Jul. 12, 2007

Related U.S. Application Data

(60) Provisional application No. 60/720,809, filed on Sep. 27, 2005.

(51) Int. Cl.
*A61B 17/70* (2006.01)
(52) U.S. Cl. ....................................... 606/248
(58) Field of Classification Search ................... 606/248, 606/249
See application file for complete search history.

(56) References Cited

U.S. PATENT DOCUMENTS

| | | | |
|---|---|---|---|
| 3,648,691 A | 3/1972 | Lumb et al. | |
| 4,554,914 A | 11/1985 | Kapp et al. | |
| 4,570,618 A | 2/1986 | Wu | |
| 4,573,454 A | 3/1986 | Hoffman | |
| 4,604,995 A | 8/1986 | Stephens et al. | |
| 4,686,970 A | 8/1987 | Dove et al. | |
| 4,790,297 A | 12/1988 | Luque | |
| 4,887,595 A | 12/1989 | Heinig et al. | |
| 5,011,484 A | 4/1991 | Breard | |
| 5,366,455 A * | 11/1994 | Dove et al. | 606/250 |
| 5,375,823 A | 12/1994 | Navas | |
| 5,415,661 A | 5/1995 | Holmes | |
| 5,496,318 A | 3/1996 | Howland et al. | |
| 5,540,688 A | 7/1996 | Navas | |
| 5,609,634 A | 3/1997 | Voydeville | |
| 5,645,599 A | 7/1997 | Samani | |
| 5,672,175 A | 9/1997 | Martin | |
| 5,725,582 A | 3/1998 | Bevan et al. | |
| 5,733,284 A | 3/1998 | Martin | |
| 5,810,815 A * | 9/1998 | Morales | 606/250 |
| 5,836,948 A | 11/1998 | Zucherman et al. | |

(Continued)

FOREIGN PATENT DOCUMENTS

EP  0269268 A1  6/1988
(Continued)

OTHER PUBLICATIONS

Partial International Search Report for International Application No. PCT/US2006/037401 mailed Feb. 19, 2007.

(Continued)

*Primary Examiner* — Ellen C Hammond
(74) *Attorney, Agent, or Firm* — Tram Anh Nguyen

(57) ABSTRACT

The present invention provides interspinous vertebral and lumbosacral stabilization devices, and methods of using these devices for treating spinal instability conditions. The invention includes interspinous vertebral stabilization devices adapted for placement between the spinous processes of two or more adjacent vertebrae. The invention also includes lumbar stabilization devices adapted to be placed between a lumbar vertebra and an adjacent vertebra, including the first sacral vertebra (S1), to stabilize the lumbosacral region of a patient, and method for using such devices.

18 Claims, 14 Drawing Sheets

U.S. PATENT DOCUMENTS

| | | | |
|---|---|---|---|
| 5,860,977 A | 1/1999 | Zucherman et al. | |
| 5,876,404 A | 3/1999 | Zucherman et al. | |
| 5,951,553 A | 9/1999 | Betz et al. | |
| 5,961,516 A | 10/1999 | Graf | |
| 5,984,967 A * | 11/1999 | Zdeblick et al. | 623/17.16 |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,267,764 B1 | 7/2001 | Elberg | |
| 6,273,914 B1 | 8/2001 | Papas | |
| 6,280,444 B1 | 8/2001 | Zucherman et al. | |
| 6,312,431 B1 | 11/2001 | Asfora | |
| 6,332,882 B1 | 12/2001 | Zucherman et al. | |
| 6,332,883 B1 | 12/2001 | Zucherman et al. | |
| 6,364,883 B1 | 4/2002 | Santilli | |
| 6,379,355 B1 | 4/2002 | Zucherman et al. | |
| 6,402,750 B1 | 6/2002 | Atkinson et al. | |
| 6,419,676 B1 | 7/2002 | Zucherman et al. | |
| 6,419,677 B2 | 7/2002 | Zucherman et al. | |
| 6,436,099 B1 | 8/2002 | Drewry et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,761,720 B1 | 7/2004 | Senegas | |
| 6,796,983 B1 | 9/2004 | Zucherman et al. | |
| 6,852,128 B2 | 2/2005 | Lange | |
| 6,875,212 B2 | 4/2005 | Shaolian et al. | |
| 6,899,713 B2 | 5/2005 | Shaolian et al. | |
| 6,902,566 B2 | 6/2005 | Zucherman et al. | |
| 7,163,558 B2 * | 1/2007 | Senegas et al. | 623/17.11 |
| 7,604,652 B2 * | 10/2009 | Arnin et al. | 606/249 |
| 7,658,752 B2 * | 2/2010 | Labrom et al. | 606/249 |
| 2003/0153915 A1 | 8/2003 | Nekozuka et al. | |
| 2003/0171749 A1 | 9/2003 | Le Couedic et al. | |
| 2003/0191470 A1 | 10/2003 | Ritland | |
| 2003/0216736 A1 | 11/2003 | Robinson et al. | |
| 2004/0073215 A1 | 4/2004 | Carli | |
| 2004/0106995 A1 | 6/2004 | Le Couedic et al. | |
| 2004/0153071 A1 | 8/2004 | Zucherman et al. | |
| 2004/0153072 A1 | 8/2004 | Bonutti | |
| 2004/0162617 A1 | 8/2004 | Zucherman et al. | |
| 2004/0181282 A1 | 9/2004 | Zucherman et al. | |
| 2004/0199255 A1 | 10/2004 | Mathieu et al. | |
| 2004/0220568 A1 | 11/2004 | Zucherman et al. | |
| 2004/0243239 A1 | 12/2004 | Taylor | |
| 2005/0010293 A1 | 1/2005 | Zucherman et al. | |
| 2005/0010298 A1 | 1/2005 | Zucherman et al. | |
| 2005/0033434 A1 * | 2/2005 | Berry | 623/17.14 |
| 2005/0056979 A1 | 3/2005 | Studer et al. | |
| 2005/0065514 A1 | 3/2005 | Studer | |
| 2005/0075634 A1 | 4/2005 | Zucherman et al. | |
| 2005/0101955 A1 | 5/2005 | Zucherman et al. | |
| 2005/0113927 A1 | 5/2005 | Malek | |
| 2005/0143738 A1 | 6/2005 | Zucherman et al. | |
| 2005/0165398 A1 | 7/2005 | Reiley | |
| 2005/0196420 A1 | 9/2005 | Zucherman et al. | |
| 2005/0203512 A1 | 9/2005 | Hawkins et al. | |
| 2005/0203624 A1 | 9/2005 | Serhan et al. | |
| 2005/0209603 A1 | 9/2005 | Zucherman et al. | |
| 2005/0216017 A1 | 9/2005 | Fielding et al. | |
| 2005/0228383 A1 | 10/2005 | Zucherman et al. | |
| 2005/0228384 A1 | 10/2005 | Zucherman et al. | |
| 2006/0015181 A1 * | 1/2006 | Elberg | 623/16.11 |
| 2006/0036240 A1 * | 2/2006 | Colleran et al. | 606/61 |
| 2006/0142759 A1 * | 6/2006 | Arnin et al. | 606/61 |
| 2006/0241601 A1 * | 10/2006 | Trautwein et al. | 606/61 |
| 2006/0241610 A1 * | 10/2006 | Lim et al. | 606/69 |
| 2006/0282079 A1 * | 12/2006 | Labrom et al. | 606/61 |
| 2006/0293662 A1 * | 12/2006 | Boyer et al. | 606/61 |
| 2008/0114358 A1 * | 5/2008 | Anderson et al. | 606/64 |
| 2008/0215094 A1 * | 9/2008 | Taylor | 606/246 |

FOREIGN PATENT DOCUMENTS

| | | |
|---|---|---|
| EP | 0 322 334 | 6/1989 |
| EP | 0 649 636 | 4/1995 |
| EP | 1 138 268 | 10/2001 |
| EP | 1 330 987 | 7/2003 |
| EP | 1924210 A2 | 5/2008 |
| FR | 2 703 239 | 10/1994 |
| FR | 2 717 675 | 9/1995 |
| FR | 2858929 A1 | 2/2005 |
| WO | WO 94/17736 A1 | 8/1994 |
| WO | WO 94/26192 | 11/1994 |
| WO | WO 99/40866 | 8/1999 |
| WO | WO 01/45576 A1 | 6/2001 |
| WO | WO 01/56489 A1 | 8/2001 |
| WO | WO 02/102259 A2 | 12/2002 |
| WO | WO 03/026521 A1 | 4/2003 |
| WO | WO 2004/024010 A1 | 3/2004 |
| WO | 2004039283 A2 | 5/2004 |
| WO | WO 2004/073533 A1 | 9/2004 |
| WO | WO 2004/084743 A1 | 10/2004 |
| WO | WO 2005/009300 A1 | 2/2005 |
| WO | 2006110578 A2 | 10/2006 |

OTHER PUBLICATIONS

International Search Report for International Application No. PCT/US2006/037401 mailed Jun. 19, 2007.

Written Opinion of the International Searching Authority for International Application No. PCT/US2006/037401 mailed Jun. 19, 2007.

Extended European Search Report for European Patent Application EP 11 165 091.7 Based on International Patent Application PCT/US2006/037401 Dated December 21, 2011.

* cited by examiner

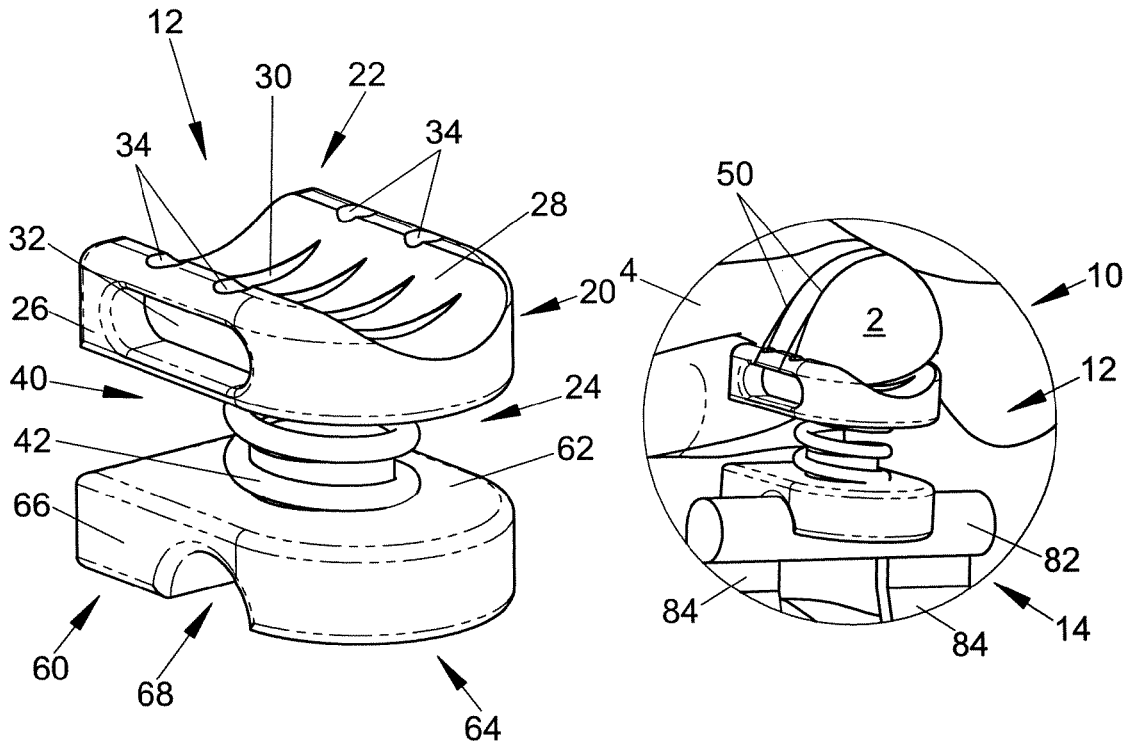
FIG. 1A
FIG. 1C
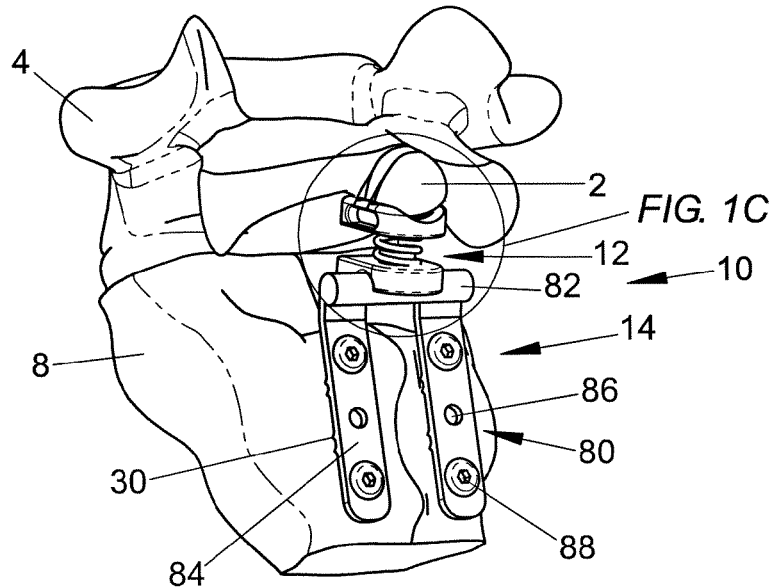
FIG. 1B

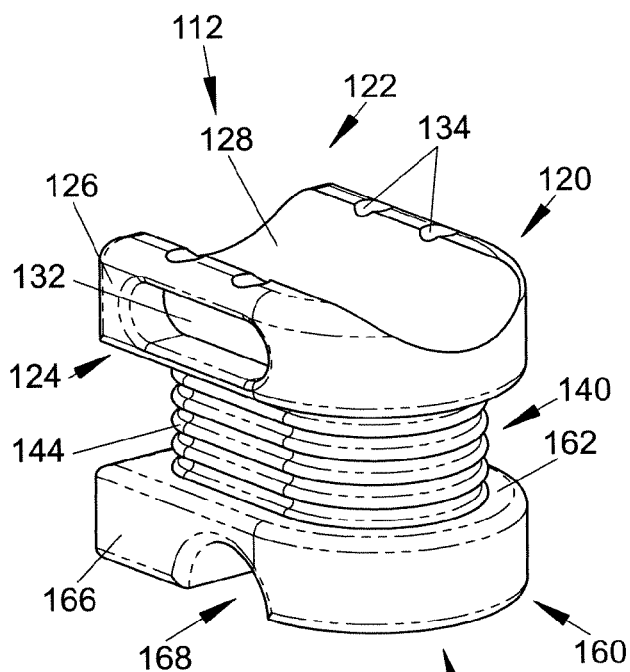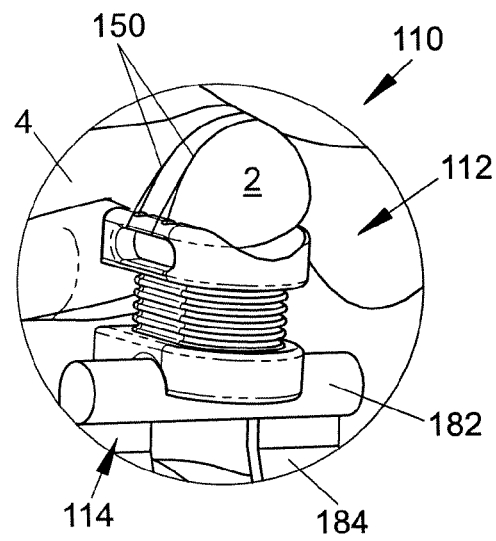
FIG. 2A
FIG. 2C
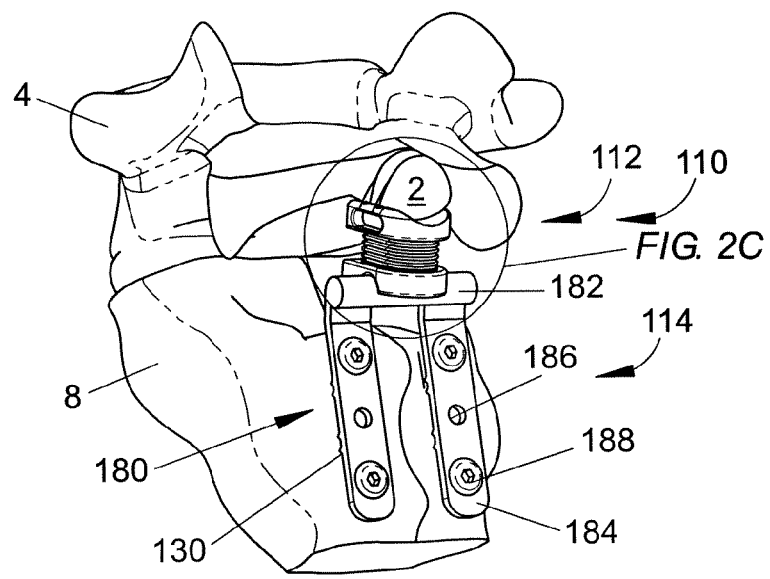
FIG. 2B

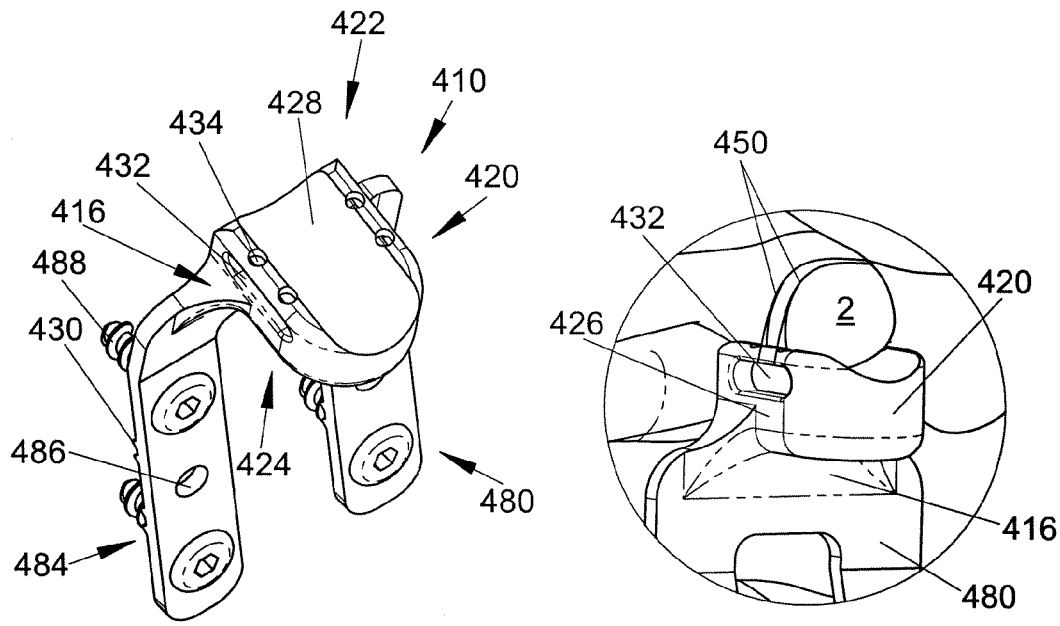
FIG. 12A
FIG. 12C
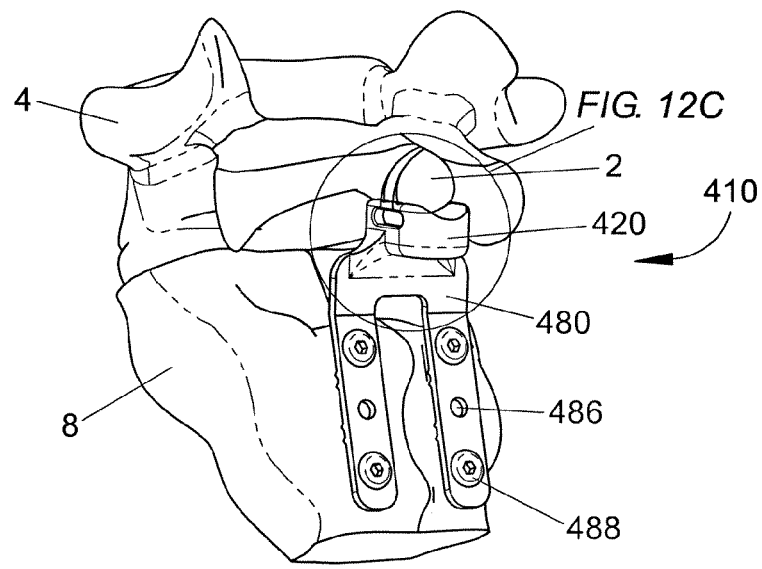
FIG. 12B

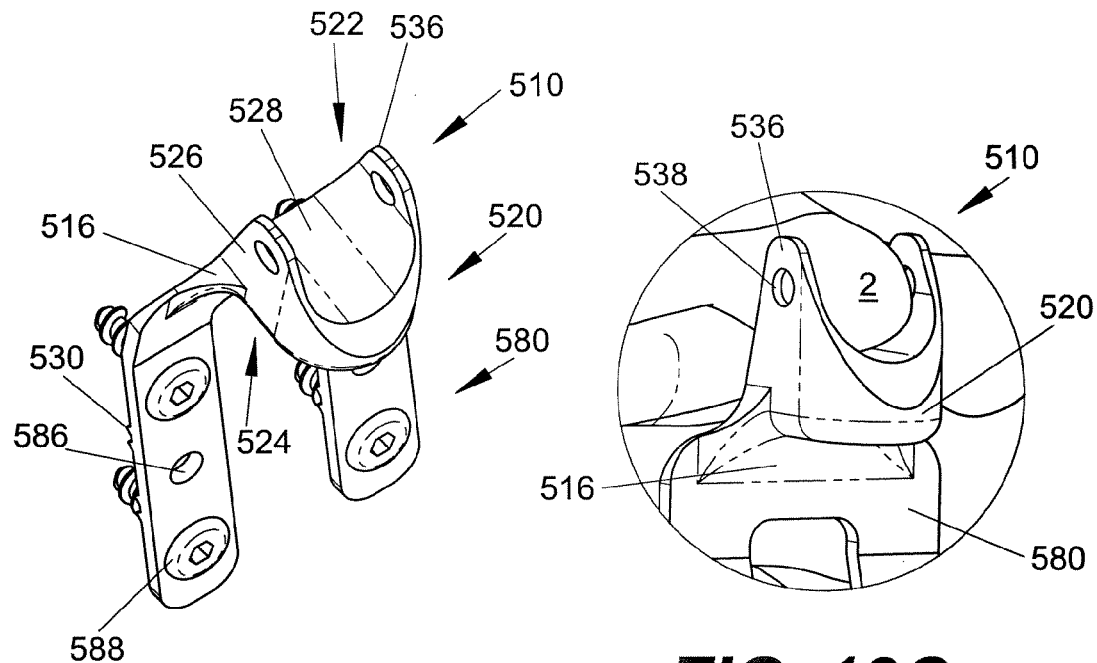
FIG. 13A
FIG. 13C
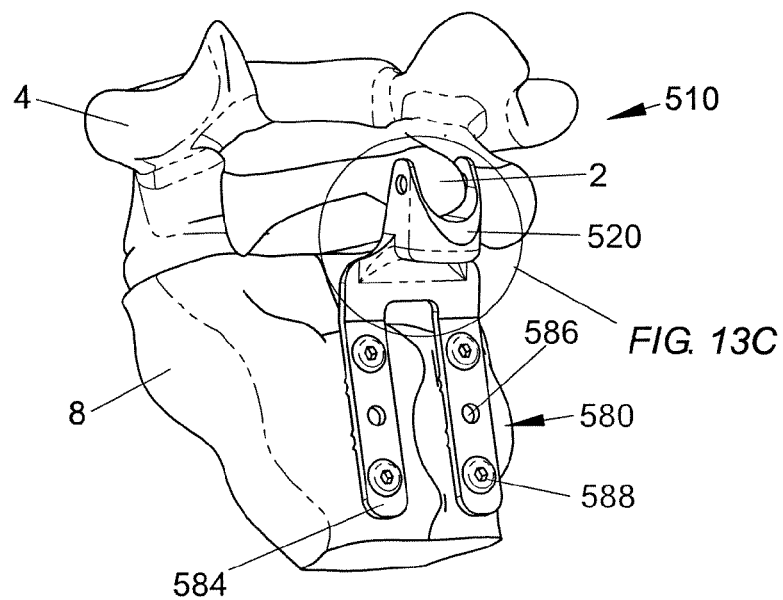
FIG. 13B

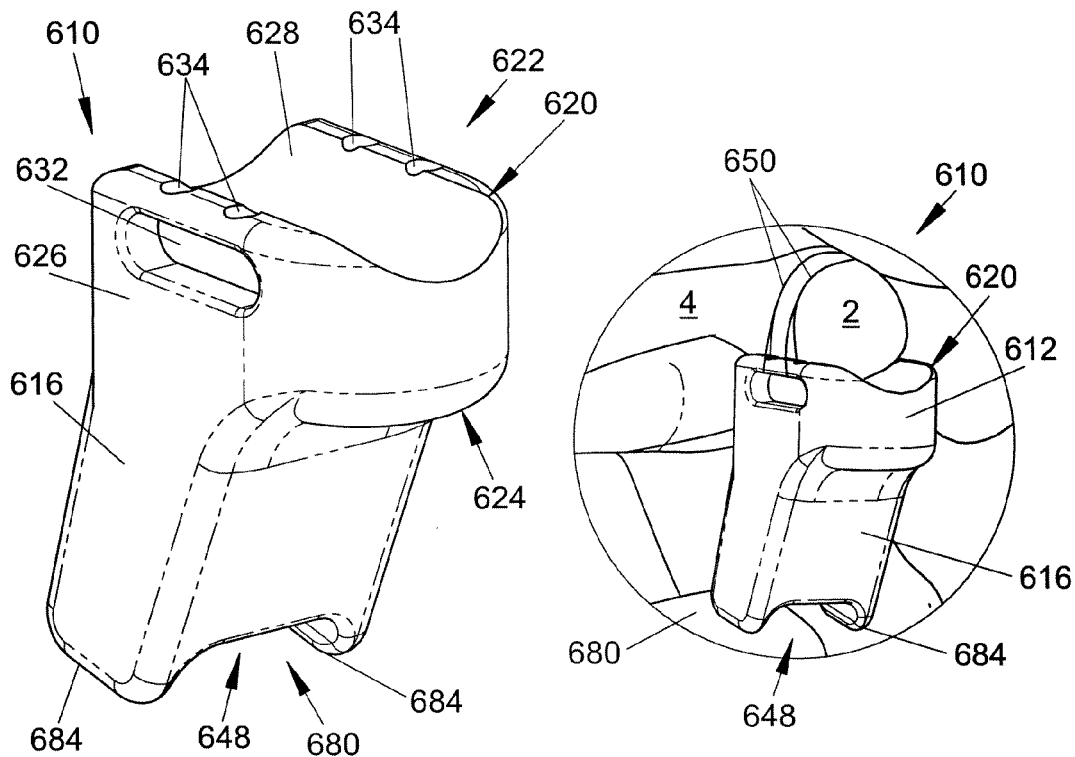
FIG. 14A
FIG. 14C
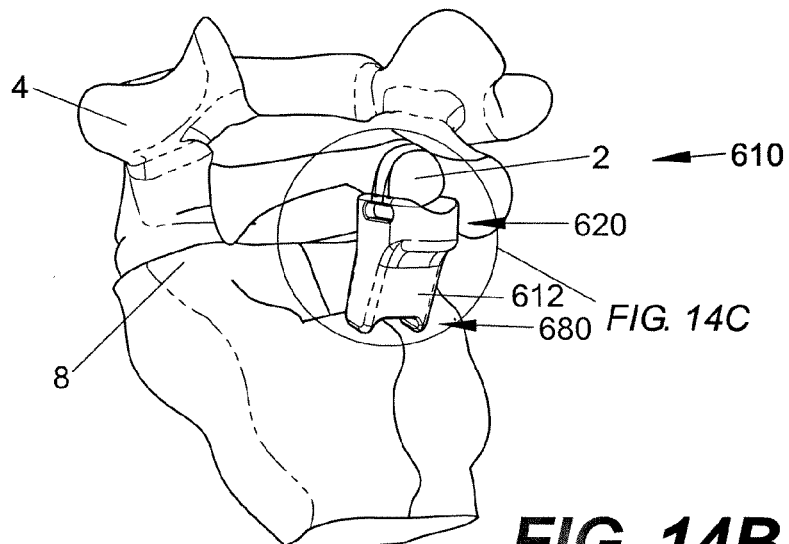
FIG. 14B

INTERSPINOUS VERTEBRAL STABILIZATION DEVICES

This application claims benefit of U.S. Provisional Application No. 60/720,809, filed Sep. 27, 2005, the contents of which are incorporated herein by reference.

FIELD OF THE INVENTION

The present invention relates to devices and methods for treating spinal conditions, and specifically to vertebral stabilization devices and methods of using such devices for stabilizing adjacent vertebrae. More specifically, the present invention relates to interspinous vertebral stabilization devices for placement between the spinous processes of two or more vertebrae, and including lumbosacral stabilization devices for placement between a lumbar vertebra and an adjacent vertebra, and methods of using such devices.

BACKGROUND OF THE INVENTION

Diseases of the spine cause significant morbidity. These diseases include abnormalities of the vertebrae, the intervertebral discs, the facet joints, and connective tissue around the spine. These abnormalities can be due to a number of causes, including mechanical injury or degenerative disc disease. Such abnormalities can cause instability to the spine, allowing the vertebral column to become misaligned and producing micromotion between adjacent vertebrae. Vertebral misalignment and micromotion may result in wear to the vertebral bony surfaces and ultimately cause severe pain. Further, these conditions are often chronic and progressive problems.

The treatments for spinal disorders may include long-term medical management or surgery. Medical management is generally directed at controlling the symptoms, such as pain, rather than correcting the underlying problem. For some patients, this may require chronic use of pain medications, which may alter patient mental state or cause other negative side effects.

Another treatment option is surgery, which is often highly invasive and may significantly alter the spinal anatomy and function. For example, one surgical treatment for certain spinal conditions includes spinal fusion, whereby two or more vertebrae may be joined using bone grafts and/or synthetic implants. The fusion process is irreversible and may significantly alter vertebral range-of-motion. Further, current surgical procedures are often only applicable to patients in a significantly-progressed disease state.

Consequently, spinal surgeons have begun to develop more advanced surgical procedures and spinal stabilization and/or repair devices that are less invasive, may be reversible, and cause a less drastic alteration in the patient's normal anatomy and spinal function. These procedures may be used in an earlier stage of disease progression and, in some situations, may even stop or reverse disease progression.

Recently, a variety of interspinous stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Current interspinous vertebral implants are configured to be attached to the spinous processes of two or more adjacent vertebrae. Because the sacrum has a very small or non-existent spinous process, these devices cannot be implanted, for instance, between the fifth lumbar vertebra (L5) and the first sacral vertebra (S1). However, many patients have spinal conditions that affect the L5 and sacral vertebrae. It would therefore be desirable to provide improved interspinous vertebral stabilization devices, and in particular, devices that can be implanted between the sacrum and a lumbar vertebra.

SUMMARY OF THE INVENTION

The present invention provides interspinous vertebral and lumbosacral stabilization devices, and methods of using these devices for treating spinal instability conditions. The invention includes interspinous vertebral stabilization devices configured for placement between the spinous processes of two or more adjacent vertebrae. The invention also provides lumbosacral stabilization devices adapted to be placed between a lumbar vertebra and an adjacent vertebra, including the first sacral vertebra (S1), to stabilize the lumbosacral region of a patient, and method for using such devices.

One aspect of the invention provides an implantable interspinous stabilization device for stabilizing adjacent vertebrae or a lumbar vertebra near a sacrum. The device may comprise a flexible body including a first portion having a bone-contacting region configured for placement beneath a spinous process of a vertebra. The device may further include a second, base portion constructed to cooperate with a bone attachment member, the bone attachment member being configured to secure the device to a bony surface of an adjacent vertebra. A flexible element connecting the first and second portions may also be included. In certain exemplary embodiments, the flexible element can be, for example, a spring or a cushion.

A second aspect of the invention provides an implantable device for stabilizing a lumbar region of a patient. The implantable device includes a bracket for stabilizing a lumbar vertebra. The bracket includes a platform for placement under a spinous process of the lumbar vertebra. An anchor portion extends from the platform for securing the bracket between the lumbar vertebra and a sacrum. In certain exemplary embodiments, the platform can be laterally extending with respect to the anchor portion. The bracket can be constructed to be rigid or semi-rigid if a limited degree of flexibility (i.e., compression/extension) is desired.

A third aspect of the invention provides an implantable interspinous stabilization device. The device includes a bracket including a body having a scaffold portion at a first end. The scaffold portion includes a contoured bone-contacting region for placement of a spinous process of a vertebra thereon. At an opposite end is a bone-attachment portion. The bone-attachment portion can be configured to secure the device to a bony surface of an adjacent vertebra, such as a sacrum.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several exemplary embodiments of the invention and together with the description, serve to explain the principles of the invention.

BRIEF DESCRIPTION OF THE DRAWINGS

FIG. 1A illustrates a perspective view of an exemplary embodiment of an implantable device according to this invention.

FIG. 1B provides a perspective view of an assembled device of FIG. 1A in situ.

FIG. 1C shows an enlarged view of the implanted device of FIG. 1B.

FIG. 2A illustrates a perspective view of an implantable device, according to another exemplary disclosed embodiment.

FIG. 2B illustrates a perspective view of the assembled device of FIG. 2A in situ.

FIG. 2C shows an enlarged view of the implanted device of FIG. 2B.

FIG. 5A illustrates a perspective view of the implantable device of FIG. 4 with a locking cap, according to another exemplary disclosed embodiment.

FIG. 5C shows an enlarged view of the implanted device of FIG. 5B.

FIG. 12A illustrates a perspective view of an implantable device, according to still another exemplary disclosed embodiment.

FIG. 12B provides a perspective view of the assembled device of FIG. 12A in situ.

FIG. 12C shows an enlarged view of the implanted device of FIG. 12B.

FIG. 13A illustrates a perspective view of an implantable device, according to yet still another exemplary disclosed embodiment.

FIG. 13B provides a perspective view of the assembled device of FIG. 13A in situ.

FIG. 13C shows an enlarged view of the implanted device of FIG. 13B.

FIG. 14A illustrates a perspective view of an implantable device, according to even still another exemplary disclosed embodiment.

FIG. 14B provides a perspective view of the assembled device of FIG. 14A in situ.

FIG. 14C shows an enlarged view of the implanted device of FIG. 14B.

DESCRIPTION OF THE EMBODIMENTS

Figure 3B:
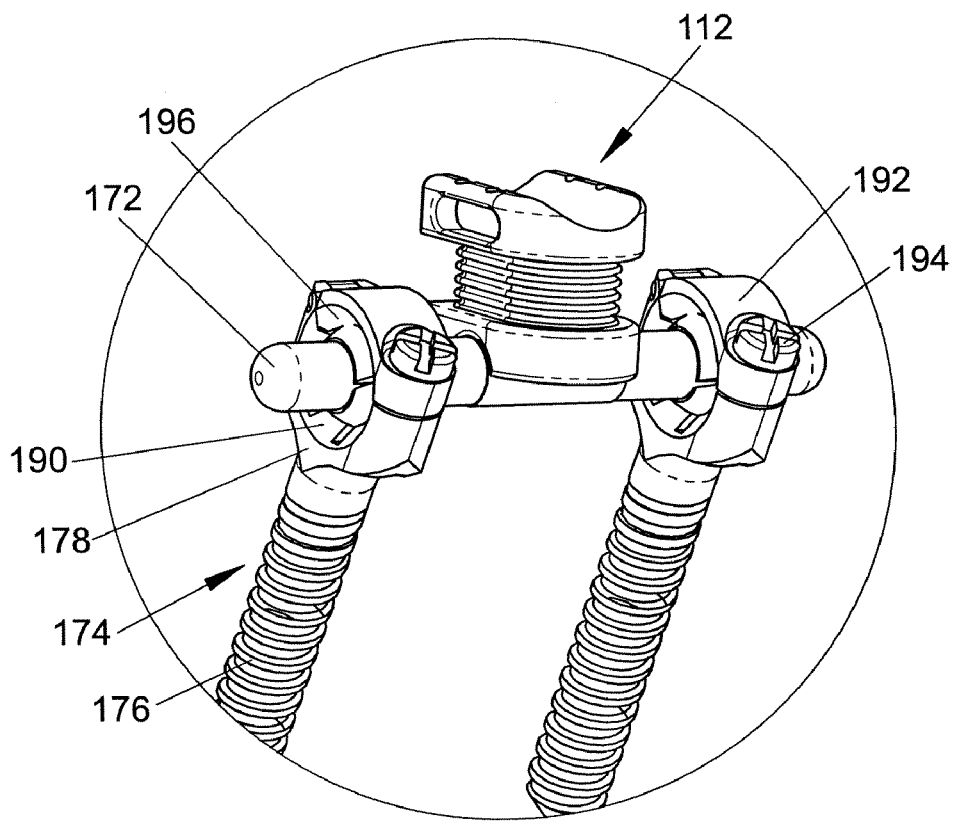
FIG. 3B shows an enlarged view of the implanted device of FIG. 3A.

Reference will now be made in detail to the exemplary embodiments of the invention, examples of which are illustrated in the accompanying drawings. Wherever possible, the same reference numbers will be used throughout the drawings to refer to the same or like parts.

The present disclosure provides implantable devices for stabilizing vertebrae when placed between the spinous processes of adjacent vertebrae, and for stabilizing the lumbosacral region of a patient by placement of the device between a lumbar vertebra and an adjacent vertebra, such as the sacrum. As shown in an exemplary embodiment depicted in FIGS. 1A-1C, the implantable device 10 can include a spacer or support body 12 that is configured to be implanted between the spinous process 2 of a lumbar vertebra 4, such as the fifth lumbar (L5) spinous process, and an adjacent vertebra. An anchor member 14 can be provided to secure the support body 12 to the adjacent vertebra, which can be, for example, the sacrum 8. When implanted, the device 10 can help with alignment of the spinal column by maintaining the vertebra 4 and its spinous process 2 in the proper spatial relationship with respect to adjacent vertebrae, thereby reducing stress on the intervertebral disc.

In one exemplary embodiment, the body 12 may include a first member 20 configured for placement beneath a spinous process 2, which can serve as a scaffold or cradle to stabilize the spinous process 2. The first member 20 can include an upper surface 22, a lower surface 24, and a sidewall 26 extending in between. The upper surface 22 can include a bone-contacting region 28 for placement of the spinous process 2 thereon. In the illustrated embodiment, the bone-contacting region 28 may comprise, for example, a contoured surface defining a saddle region. The bone-contacting region 28 may further include surface features, such as for example, barbs, surface roughening or teeth 30, as shown, to enhance its ability to grip the bony surface of the spinous process 2. Surface features may also include bioactive coatings, such as for example, porous coatings containing biologically active material that promotes bone tissue growth. These surface features may appear on any component of the implantable device 10.

Channels 32 may be formed along the sidewall 26 and extend into openings 34 at the upper surface 22, as shown in FIG. 1A. In one exemplary embodiment, one channel 32 may be formed on each lateral side of the first member 20. Optionally, however, a single channel 32 may be provided that extends across the first member 20 and opens up at both of the lateral sides. The channels 32 and openings 34 enable a flexible fixation element 50, such as for example, a wire, ligament, band, fabric webbing, or suture formed of a metallic, polymeric, synthetic, or natural material, and composites thereof, to be passed through the first member 20 and tied around the spinous process 2, thereby securing the bone to the device 10 as shown in FIGS. 1B and 1C.

The first member 20 may be attached to a second, base member 60 by a linking member 40. The second member 60 may include an upper surface 62, lower surface 64, and a sidewall 66 extending in between. The linking member 40 may extend at one end from the lower surface 24 of the first member 20 to a second end on the upper surface 62 of the second, base member 60. In one exemplary embodiment, the linking member 40 may be flexible (i.e., compressible and/or extendable) to provide the spinous process 2 with a certain limited degree of movement after the device 10 has been implanted. In the exemplary embodiment shown in FIGS. 1A-1C, the linking member 40 may take the form of a spring 42, which would enable a vertebra 4 attached to the spinous process 2 to flex, rotate, and/or laterally bend in a controlled manner to accommodate patient movement.

The second, base member 60 may cooperate with an anchor member 14 for securing the implantable device 10 to the patient. As shown in FIGS. 1B and 1C, the lower surface 64 of the second, base member 60 may include a channel or groove 68 extending across the base member 60. The anchor member 14 may take the form of, for example, a detachable bone plate 80 having a rod-shaped attachment end 82 that is configured to be held within the groove 68 of the base member 60. In one exemplary embodiment, the groove 68, having a C-shape, allows the bone plate 80 to be snap-fitted onto the base member 60 and still be rotatable, thereby providing an adjustable joint between the support body 12 and the anchor member 14. This flexibility provides a greater degree of freedom for the surgeon to be able to adjust the bone plate 80 as needed during implantation. Further, the adjustable, rotatable joint between the support body 12 and the anchor member 14 would allow the spinous process 2 being stabilized to be even more responsive to normal patient movement. A plastic liner formed from, for example, a polyethylene such as ultra high molecular weight polyethylene (UHMWPE) or polyetheretherketone (PEEK) can be provided between the rod-like attachment end 82 and the groove 68, in order to provide smooth gliding motion of the body 12 against the plate 80.

The bone plate 80 may further include one or more extensions or legs 84 extending from the rod-like attachment end 82. As shown in FIG. 1B, two legs 84 may extend, one on each end, from the rod-like attachment end 82. Alternatively, the bone plate 80 may be formed with more than two legs 84, if desired. The legs 84 may further include fastener holes 86 for the insertion of bone fasteners, such as for example, bone screws 88, thereby enabling the secure attachment of the bone plate 80 to a bony surface such as the sacrum 8. Although screws 88 have been described, it is understood that other alternative bone fasteners such as pins, tacks, and rivets may be used with the present invention. In one exemplary embodiment, the legs 84 are positioned so as to flank the median crest when attached to the sacrum. Surface features such as, for example, a bioactive coating and/or teeth 30 may also be provided on the legs 84 to enhance attachment to the bony surface.

In one exemplary method of implanting the device 10, the spacer body 12 may be assembled to the anchor member 14 prior to implantation. In this method, the spacer body 12 can be positioned such that the spinous process 2 of the vertebra 4 to be supported rests onto the bone-contacting region 28, and the anchor member 14 is placed against the sacrum 8. Thereafter, screws 88 can be inserted through the fastener holes 86 to secure the anchor member 14 to the sacrum 8. A flexible fixation element 50 can be tied around the spinous process 2 and the first member 20 of the spacer body 12 to secure the spinous process 2 to the spacer body 12.

Alternatively, a partially assembled device 10 may be implanted. For example, the anchor member 14 may first be secured to the sacrum 8 with screws 88. Next, the spacer body 12 may be snap-fitted to the anchor member 14 and manipulated such that the spinous process 2 of the vertebra 4 to be supported rests on the bone-contacting region 28. Then, a flexible fixation element 50 can be used to secure the first member 20 of the spacer body 12 to the spinous process, as shown.

FIGS. 2A-2C illustrate an implantable device 110 similar to the device 10 of FIGS. 1A-1C, but with a flexible cushion 144 connecting the first member 120 to the second member 160. In all other respects, the devices are the same, with like elements of the device 110 having the same reference numerals as device 10, following the prefix "1". The flexible cushion 144 may comprise an elastomeric material. In one embodiment, the flexible cushion 144 may comprise a fabric cover that encloses an elastomeric material such as, for example, silicone or rubber, or a swellable material such as a hydrogel. Further, the flexible cushion 144 may be formed with pleats or crimps to facilitate compression and/or flexion, as shown in FIG. 2A. Like the spring 42, the flexible cushion 144 can enable the vertebra 4 attached to the spinous process 2 to flex, rotate, and/or laterally bend in a controlled manner to accommodate patient movement. The degree of flexibility or resistance may be controlled by selecting a material having a desired modulus of elasticity to form the linking members 40, 140, or by varying the thickness or dimensions of the linking members 40, 140 to adjust the level of resistance. Of course, various other flexible and/or conformable designs, shapes, and sizes may be utilized for the linking member 40, 140 of the present disclosure.

Figure 3A:
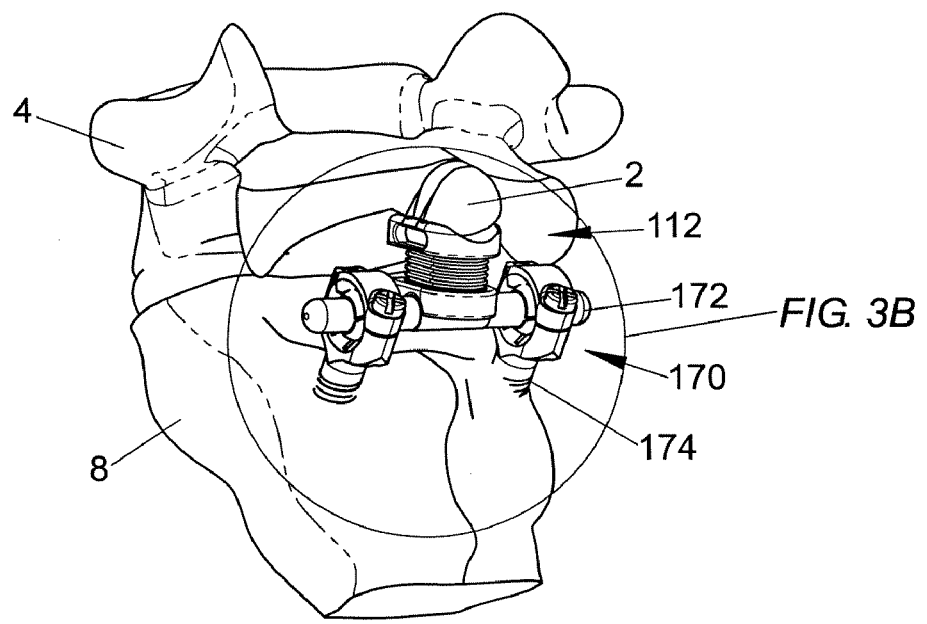
FIG. 3A illustrates a perspective view of the assembled device of FIG. 2A with a rod-based anchor system in situ, according to yet another exemplary disclosed embodiment.

Instead of attachment with a bone plate 80, 180, the spacer bodies 12, 112 of the present invention may also be secured to the patient using a rod and bone anchor system 170, as shown in FIGS. 3A and 3B. The use of a rod and bone anchor system 170 enables the implantable devices 10, 110 of the present invention to be adapted for insertion at any level of the spinal column. In particular, the rod-based systems may be used to secure a spacer body 12, 112 between any pair of adjacent vertebrae by securing the anchors of the rod to the pedicles of the vertebra adjacent to the vertebra and its spinous process being stabilized.

In one exemplary embodiment, the rod and bone anchor system 170 can include a rod 172 and at least one bone anchor 174. The bone anchor 174 can comprise, for example, a polyaxial screw. The device may be configured such that the rod 172 snaps into the channel 168 of the second, base member 160, similar in respect to the rod-like attachment end 82 of the bone plate 80. An exemplary embodiment of a bone anchor 174 suitable for use with the present invention is shown in FIGS. 3A and 3B. As illustrated, the bone anchor 174 includes an elongated threaded body 176 extending into a head portion 178. The head portion 178 includes a hollow spherical cavity 190 for receiving a connecting element such as, for example, a spherical clamp ring (not shown) that fits over the rod 172. A locking cap 192 may be slidingly received by the head portion 178 and secured thereon with a threaded screw 194. The locking cap 192 may also include a spherical cavity 196 to cooperate with the spherical clamp ring such that screwing the cap 192 onto the head portion 178 secures the bone anchor 174 to the rod 172. Although two anchors 174 are shown in FIGS. 3A and 3B, a plurality of anchors 174 may be used with any given rod 172, depending on the needs of the patient. It is also understood that a number of differently designed anchors may be used with the present invention in order to provide the surgeon with the ability to adapt to anatomical variations and secure the rod 172 to the patient in an effective manner.

Figure 4:
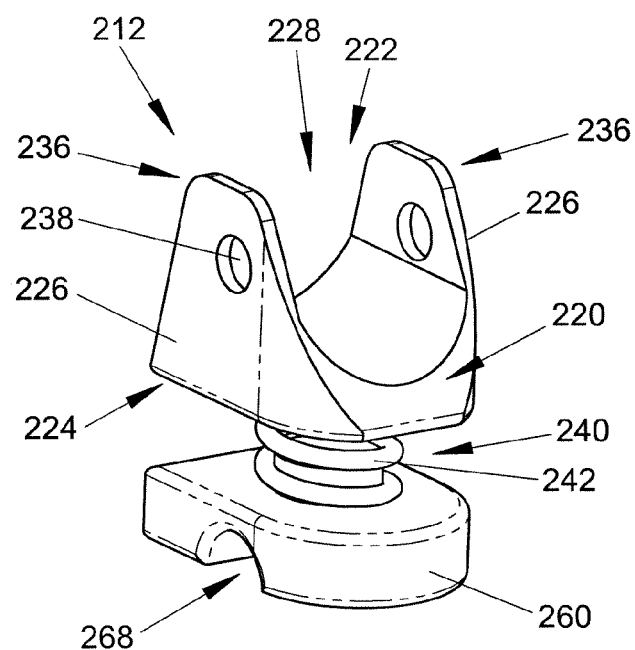
FIG. 4 illustrates a perspective view of an implantable device, according to still another exemplary disclosed embodiment.

In another exemplary embodiment, the implantable device 210 can include a spacer or support body 212, as shown in FIG. 4. The body 212 may be similar to the bodies 12, 112 of devices 10, 110, with like elements of the device 210 having the same reference numerals as device 10, following the prefix "2". As illustrated, the body 212 can include a first member 220 having raised sidewalls 226 that form wing-like projections 236. The projections 236 create a deeper saddle region 228 for seating the spinous process 2 therein, and further cradling the bone during use. Apertures or through-holes 238 may be provided on the projections 236 for attachment of a fixation device. For instance, a flexible fixation element 50, 150 such as those previously described for use with devices 10, 110 may also be applied in this embodiment to secure the spinous process 2 to the body 212.

Figure 5B:
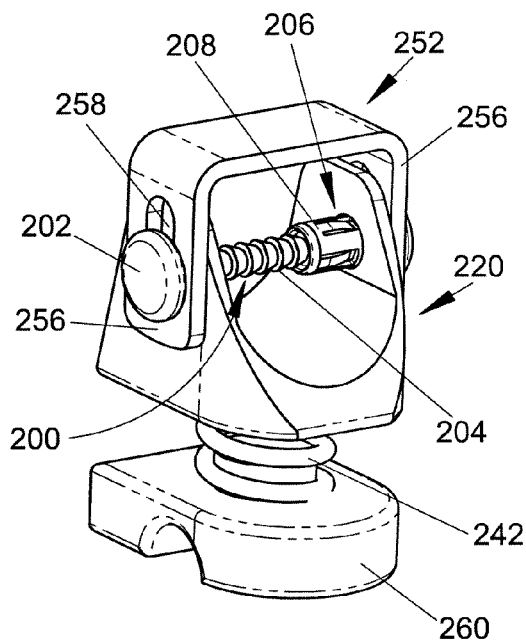
FIG. 5B provides a perspective view of the assembled device of FIG. 5A in situ.
Figure 5B:
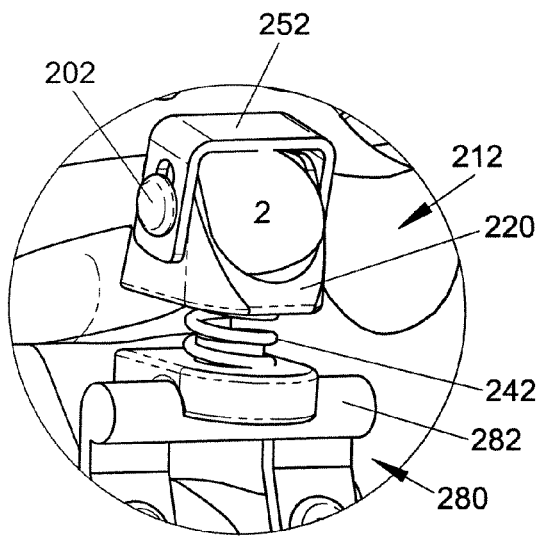
Figure 5B:
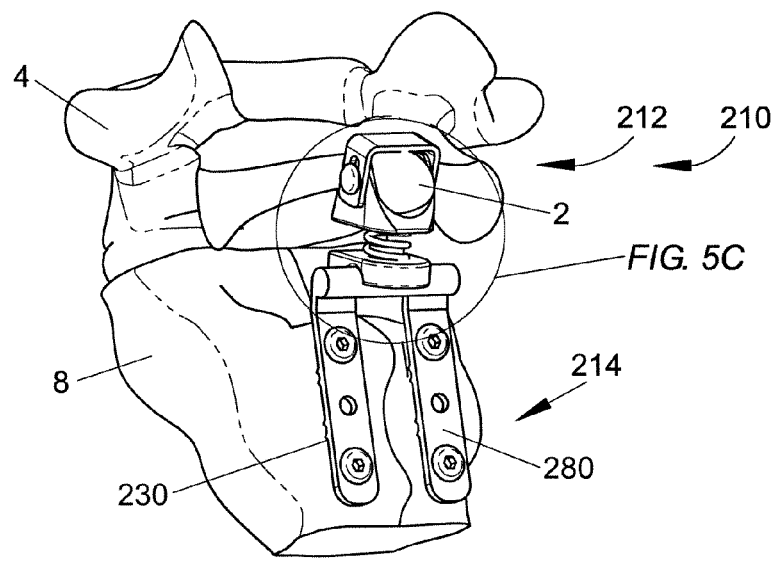

Alternatively, a rigid fixation element may also be utilized to provide an even more secure attachment of the bone to the implantable device 210. FIGS. 5A-5C illustrate the implantable device 210 in use with a locking cap 252 having a substantially U-shaped body formed by a pair of bent legs 256. The locking cap 252 can be shaped and sized as a bracket for engagement over the first member 220. Elongate slots 258 located on the legs 256 are configured to align with the through-holes 238 of the projections 236 to allow passage of a fixation element therethrough. In the exemplary embodiment illustrated in FIG. 5A, a bone fastener 200 may be inserted through the slots 258, securing together the locking cap 252, support body 212 and spinous process 2 during use. The bone fastener 200 can include a head 202 extending into an elongate threaded body 204 configured for insertion through bone tissue. To lock the bone fastener 200 in place, a cap 206 may be provided. The cap 206 may include a hollow body cavity 208 for receiving the distal end of the threaded body 204, as shown in FIG. 5A. A suitable bone fastener 200 may be found in U.S. provisional No. 60/669,346 filed on Apr. 8, 2005, the contents of which are hereby incorporated in its entirety by reference.

In other embodiments, the fixation element can comprise a laminar hook 300, which may be provided for use with the spacer or support body 212 of the present invention. In an exemplary embodiment shown in FIG. 6A, the laminar hook 300 can include a pair of legs 302 connected by a curved midsection 304. Collectively, the legs 302 and midsection 304 form a curved or wavy M-shaped body, with the midsection 304 including a U-shaped protrusion or notch, as illustrated. The legs 302 cooperate with rotating arms 310 situated on either side of the spacer body 212 to allow pivoting movement of the hook 300 with respect to the spacer body 212.

Figure 6A:
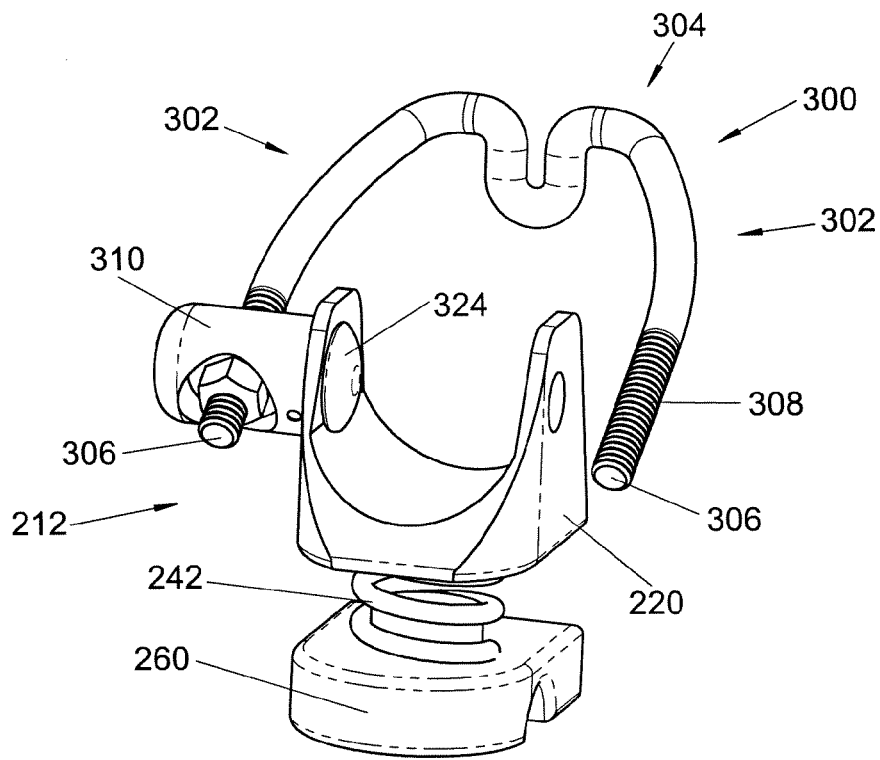
FIG. 6A shows a partially assembled view of the implantable device of FIG. 4 with a laminar hook, according to an exemplary disclosed embodiment.
Figure 6B:
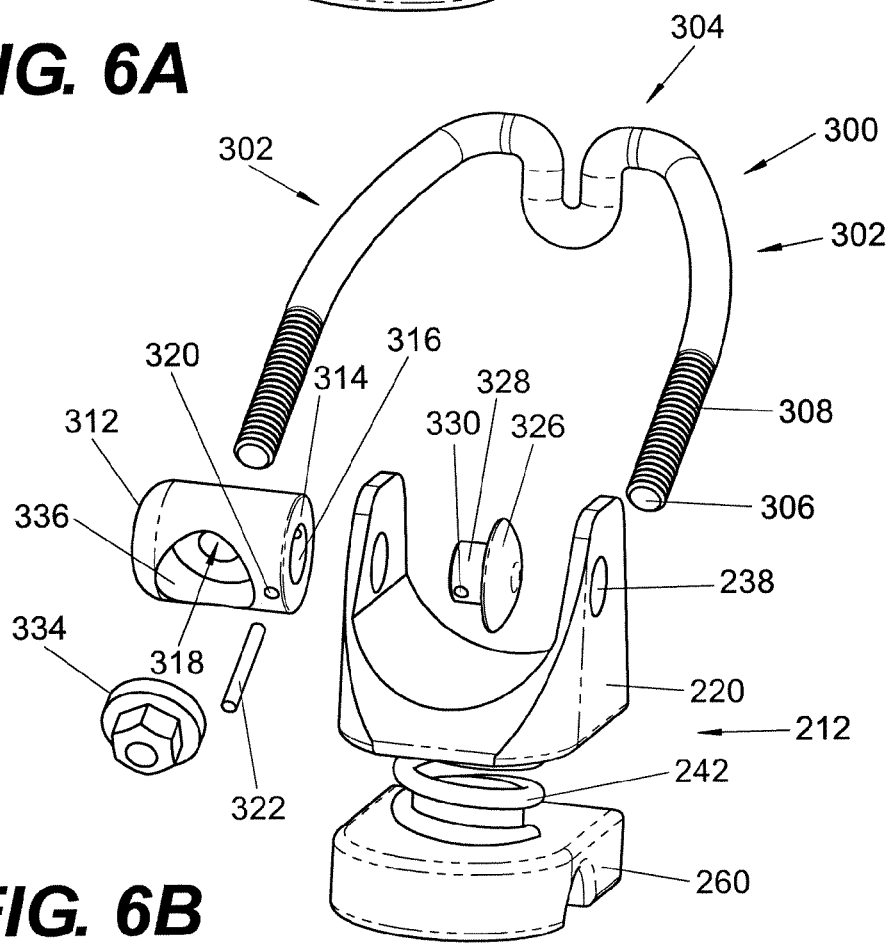
FIG. 6B shows an exploded view of the device of FIG. 6A.

As shown in FIG. 6B, the rotating arms 310 can have a generally cylindrical shape, with one closed end 312 and an opposite, open end 314 including an opening 316 extending generally parallel to the longitudinal axis of the arm 310. The closed end 312 can have a smooth, curved edge while the open end 314 can have a flat edge so as to enable flush placement against the spacer body 212. To attach each arm 310 to the support body, a locking cap 324 can be inserted through one of the apertures 238 on the spacer body 212. The locking cap 324 can include a head portion 326 and a stem portion 328, and a through-hole 330 for insertion of a pin 322 therethrough. The stem portion 328 should be sized and configured for insertion through the aperture 238 of the spacer body 212 and still be freely rotatable. An arm 310 is then placed against the stem portion 328, with the stem portion 328 fitting within the opening 316 of the arm 310 such that the spacer body 212 is sandwiched in between. Next, a pin 322 can be placed through a through-hole 320 on the arm 310, the through-hole 320 being configured to align with the through-hole 330 of the cap 324. Accordingly, the pin maintains the arm 310 and cap 324 against the spacer body 212 while allowing free rotational movement of the arm 310 and cap 324 with respect to the body 212.

To attach the laminar hook 300 to the rotating arms 310, the free ends 306 of the hook 300 can be inserted through openings 318 extending through the arms 310, the openings 318 being generally perpendicular to the longitudinal axis of the arms 310. The legs 302 of the hook 300 can include threaded portions 308 near the free ends 306 that extend beyond the arms 310 when assembled. A fastener 334, such as for example, a threaded nut can be provided to secure the legs 302 to the arms 310. The opening 318 can extend into a widened cavity 336 that would allow the fastener 334, once secured to the legs 302, to reside therein, as shown in FIG. 6A. Although a threaded connection is shown, it is contemplated that any suitable alternative connection can be provided for securing the fastener 334 to the legs 302. For example, the legs 302 can be provided with notches or grooves, while the fastener 334 can include corresponding teeth or ridges for ratcheting over the legs 302. In all cases, it is desirable to provide a mechanism for securing the hook 300 to the rotatable arms 310, which would allow the surgeon the flexibility to adjust the length of the hook 300 relative to the spacer body 212, in order to accommodate different patient anatomies.

Figure 7B:
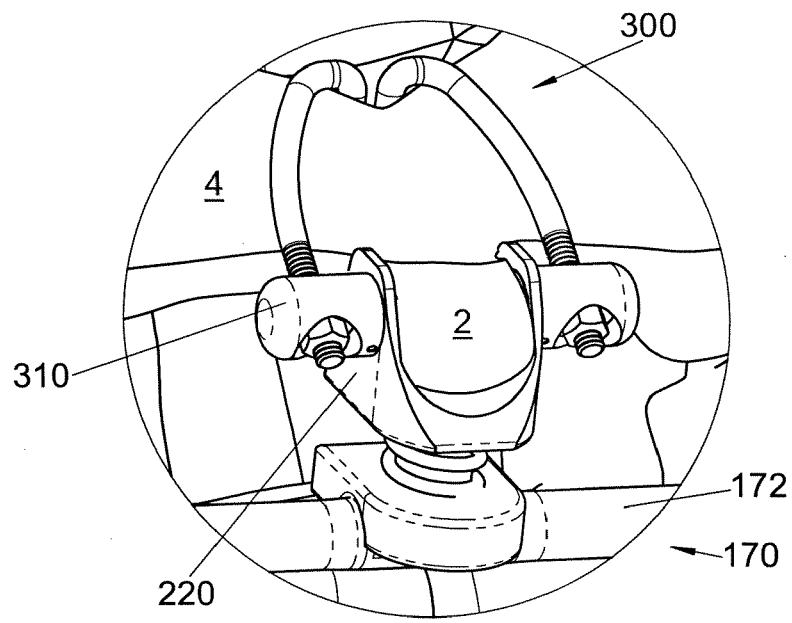
FIG. 7B shows an enlarged view of the implanted device of FIG. 7A.
Figure 7A:
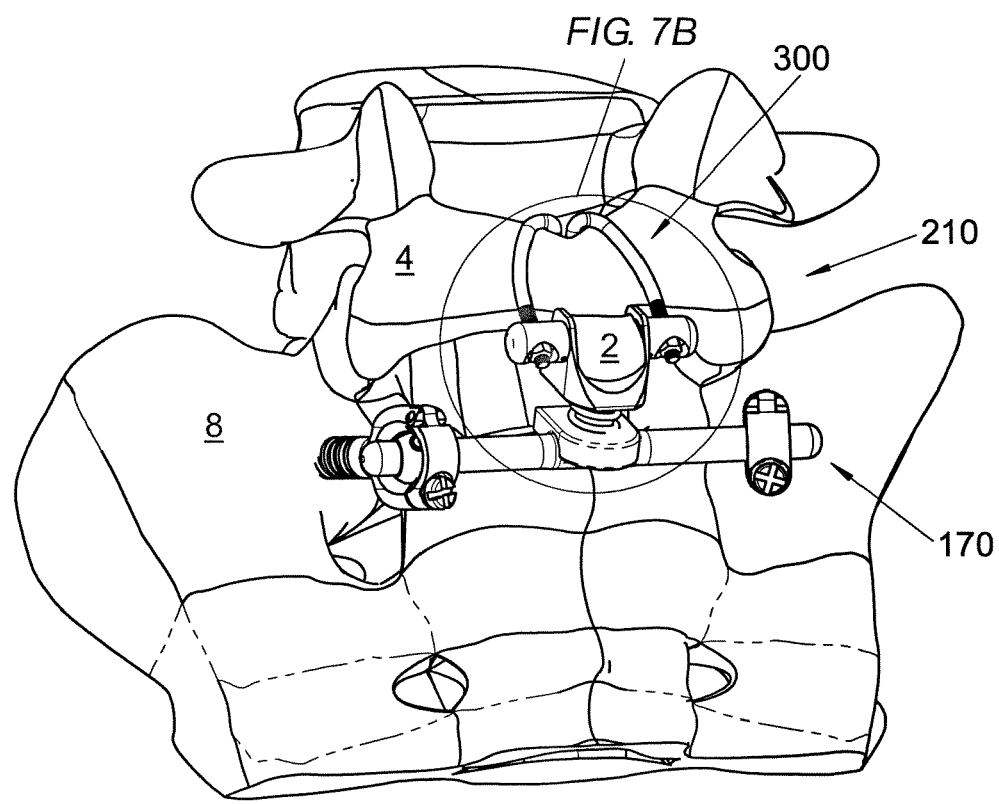
FIG. 7A provides a perspective view of the assembled device of FIG. 6A in situ.

Once fully assembled to the spacer body 212, the laminar hook 300 can assist with the positioning and attachment of the implantable device 210 to the vertebra 4. As illustrated in FIG. 7A, the implantable device 210 can be implanted between a vertebra 4 and an adjacent vertebra, such as for example, the sacrum 8. The device 210 may be attached using, for example, the bone plate 80 previously described, or a rod and screw system 170 as shown. Further, it is understood that the device 210 may be inserted between any adjacent pair of vertebrae. Once the spinous process 2 of the vertebra 4 is positioned so as to rest securely within the saddle region 228 of the spacer body 212, the laminar hook 300 can be clasped against the lamina, with the midsection 304 having the U-shaped protrusion or notch extending around the lamina. The hook 300 should be sufficiently angled or curved so as to conform to the natural anatomical curves of the lamina, as shown in greater detail in FIG. 7B.

Alternatively, the laminar hook 300 can be fully assembled after the implantable device 210 has been implanted between a pair of vertebrae. In this instance, the legs 302 can be secured to the arms 310 with the fasteners 334 after the hook 300 has been properly positioned around the lamina. Further, as previously mentioned, the surgeon can adjust the length of the hook 300 by manipulating the fastener 334 with respect to the rotatable arms 310 in order to adapt to variations in the patient's anatomy.

Figure 8A:
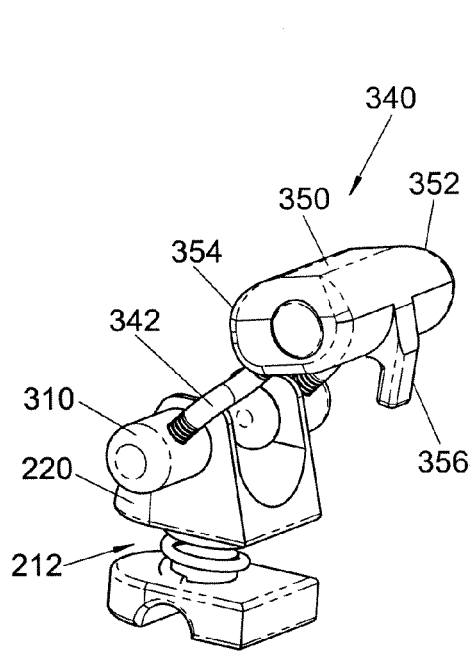
FIG. 8A illustrates a perspective view of the implantable device of FIG. 4 with a laminar hook, according to another exemplary disclosed embodiment.
Figure 8B:
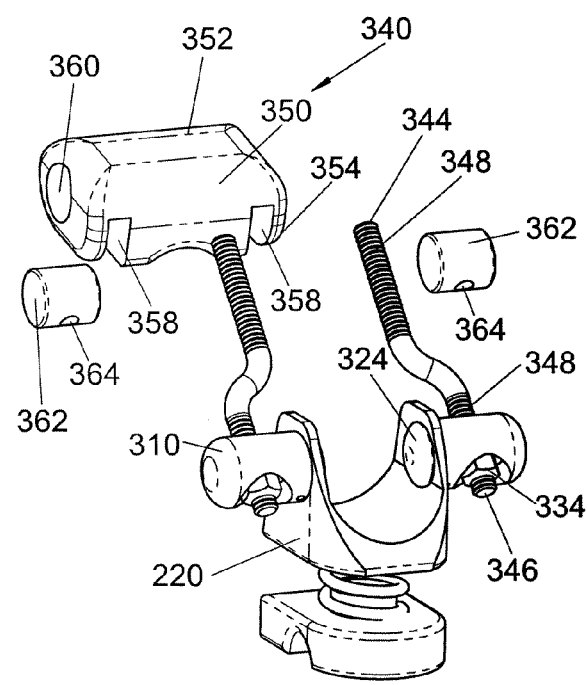
FIG. 8B shows an exploded view of the device of FIG. 8A.

In another exemplary embodiment of the present invention, a laminar hook 340 is provided which can include a pivotable head portion 350. The head portion 350 has a first end 352 from which a hook or tab 356 for grasping around the lamina can extend, as shown in FIG. 8A. The opposed, second end 354 of the head portion 350 can include slots 358 which extend into openings 360 along the sides of the head portion 350, as illustrated in FIG. 8B. To attach the laminar hook 340 onto the spacer body 212, legs 342 can be provided having threaded portions 348 near the first and second, opposed ends 344, 346. The first ends 344 of the legs 342 can be inserted into the slots 358 of the head portion 350, while the second, opposed ends 346 of the legs 342 can extend into rotatable arms 310, where the legs 342 can be secured to the arms 310 using fasteners 334, similar to the mechanism previously described for the laminar hook 300 of FIGS. 6A and 6B. Further, it is understood that the laminar hook 340 of FIGS. 8A and 8B can be similar to laminar hook 300 in all respects to the manner in which the arms 310 connect to the spacer body 212.

To enable pivotable movement of the head portion 350 with respect to the legs 342, a cylindrically-shaped bushing 362 can be provided. The bushing 362 can be configured to reside within the cylindrically shaped opening 360 along the sides of the head portion 350, and can be sized and shaped so as to allow free rotational movement within the opening 360. The bushing 362 can include a threaded hole 364 for attachment to the threaded portions 348 of the first ends 344 of the legs 342. Although a threaded connection is shown and described, it is contemplated that any suitable alternative connection can be provided for securing the fastener 334 and bushing 362 to the legs 342. For example, the legs 342 can be provided with notches or grooves, while the fastener 334 and bushing 362 can include corresponding teeth or ridges for ratcheting over the legs 342.

In one exemplary method of assembling the laminar hook 340, the bushings 362 can be placed into the openings 360 of the head portion 350. Thereafter, the legs 342 can be inserted into the slots 358, and secured to the bushings 362 by screwing the threaded portions 348 near the first ends 344 into the threaded holes 364 of the bushings 362. The free, second ends 346 of the legs 342 can then be inserted into the attached rotatable arms 310 along the sides of the spacer body 212, and secured therein with fasteners 334, such as for example, threaded nuts.

Figure 10B:
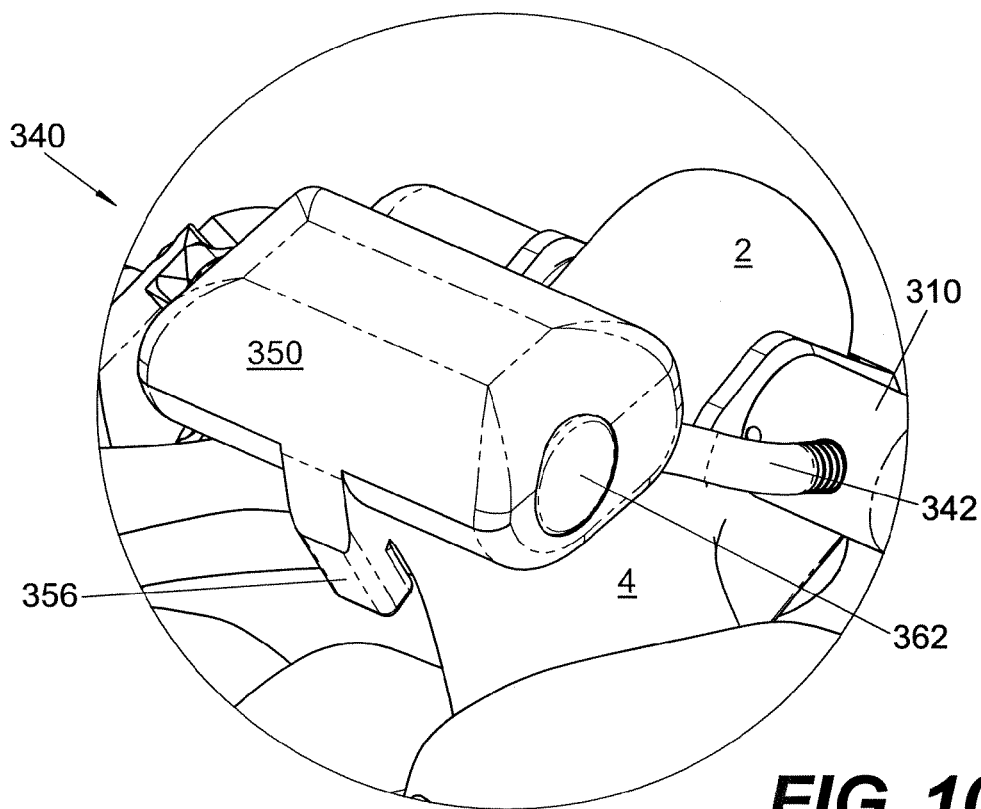
FIG. 10B shows an enlarged rear view of the implanted device of FIG. 1A.
Figure 10A:
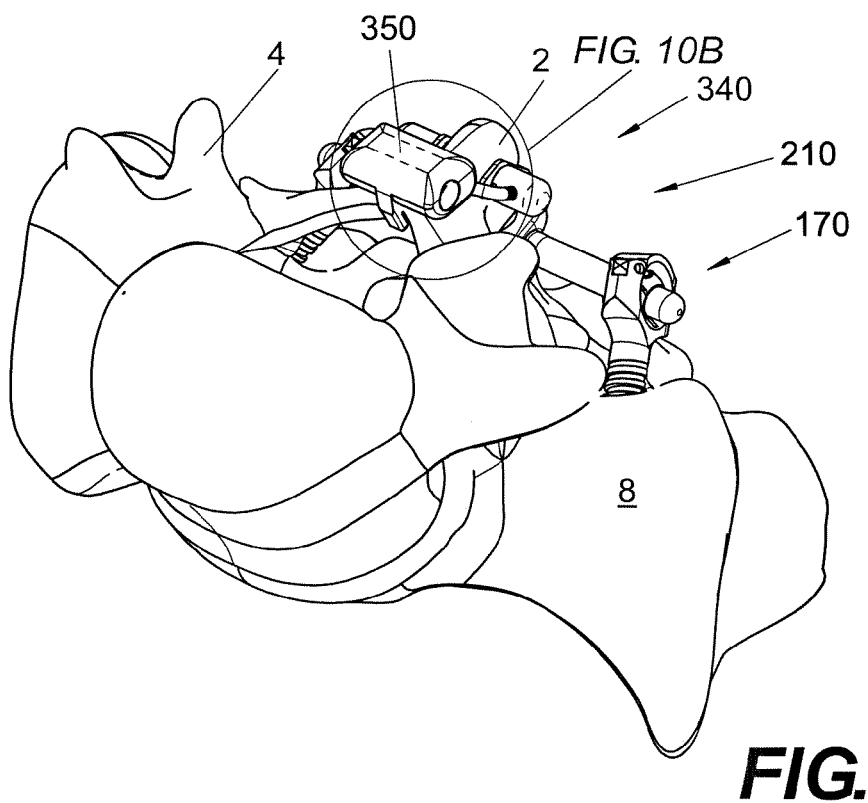
FIG. 10A illustrates a rear perspective view of the assembled device of FIG. 8A in situ.
Figure 10D:
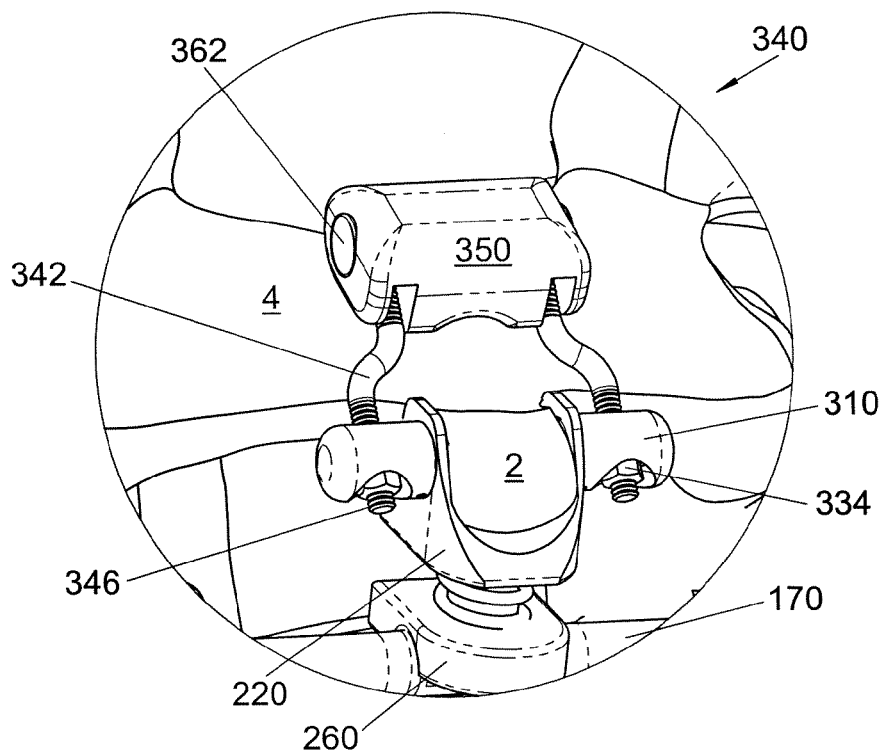
FIG. 10D shows an enlarged front view of the implanted device of FIG. 10C.
Figure 10C:
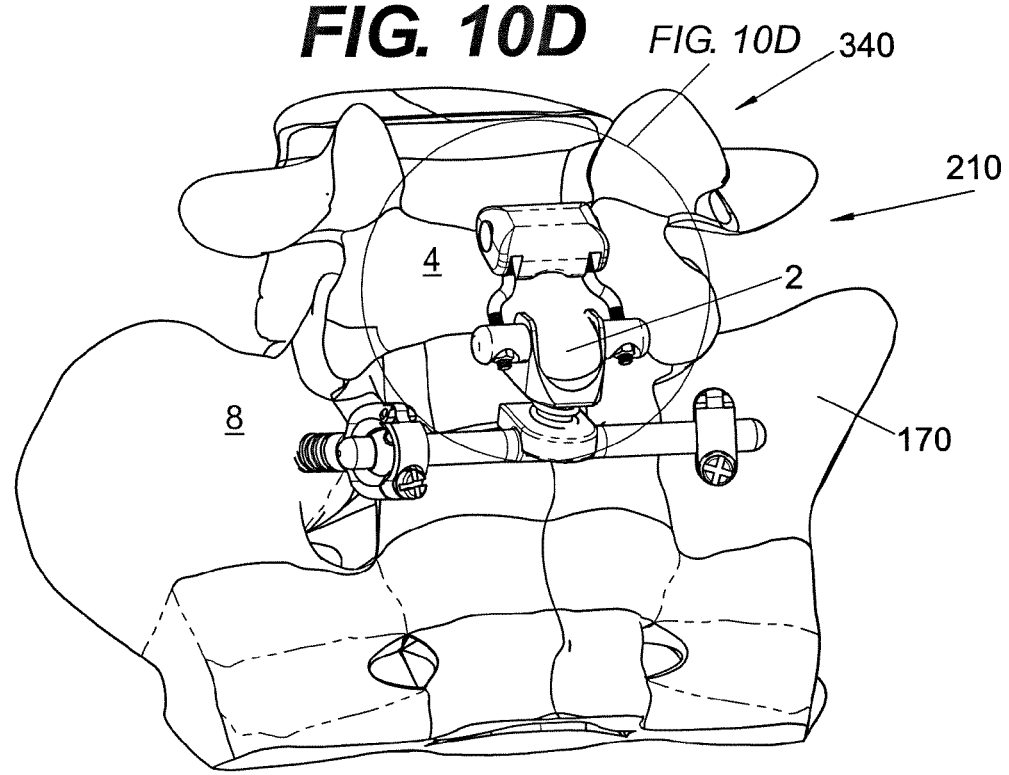
FIG. 10C illustrates a front perspective view of the assembled device of FIG. 8A in situ.

Like the previous laminar hook 300, the fully-assembled laminar hook 340 of the present embodiment can assist with the positioning and attachment of the implantable device 210 to the vertebra 4. As illustrated in FIGS. 10A and 10C, the implantable device 210 can be implanted between a vertebra 4 and an adjacent vertebra, such as for example, the sacrum 8. However, it is understood that the device 210 may be inserted between any adjacent pair of vertebrae using, for example, a rod and screw system 170 as shown. Once the spinous process 2 of the vertebra 4 is positioned within the saddle region 228 of the spacer body 212, the laminar hook 340 can be clasped onto the lamina, with the hook or tab 356 extending around the lamina, as shown in greater detail in FIG. 10B. By providing a hook 340 which is pivotable at two points (i.e., at bushings 362 and at arms 310), the hook 340 can accommodate variations in patient anatomy. Further, the legs 342 can be angled or curved so as to better conform to the natural anatomical curves of the lamina, as shown in greater detail in FIG. 10D.

The implantable device 210 can be implanted with the laminar hook 340 fully attached to the spacer body 212 as previously described. Alternatively, the laminar hook 340 can be fully attached to the spacer body 212 after the implantable device 210 has been inserted between a pair of vertebrae. In this instance, the laminar hook 340 can be partially assembled (i.e., the legs 342 are connected to the head portion 350) when the implantable device 210 (including the rotatable arms 310) is implanted. Afterwards, the legs 342 can be secured to the arms 310 with the fasteners 334 once the hook 340 has been properly positioned around the lamina. Of course, as previously mentioned, the surgeon can adjust the length of the hook 340 by manipulating the fastener 334 with respect to the rotatable arms 310 and legs 342 in order to adapt to variations in the patient's anatomy.

Figure 9A:
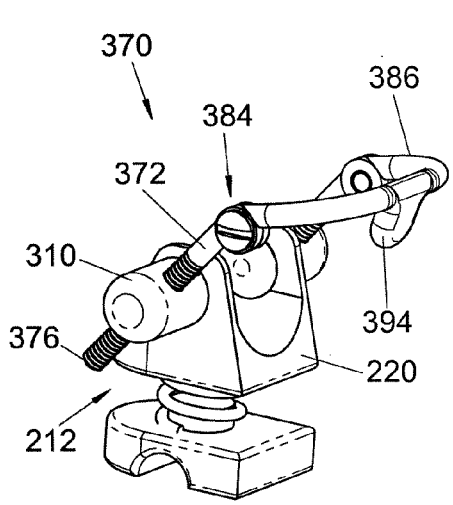
FIG. 9A illustrates a perspective view of the implantable device of FIG. 4 with a laminar hook, according to yet another exemplary disclosed embodiment.
Figure 9B:
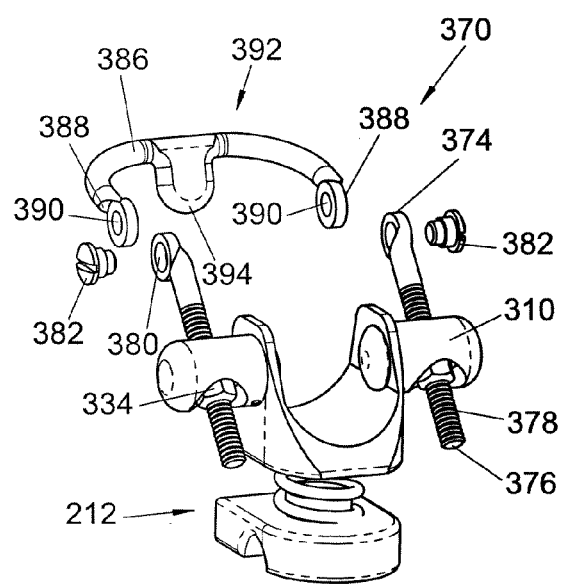
FIG. 9B shows an exploded view of the device of FIG. 9A.

Turning now to FIGS. 9A and 9B, yet another exemplary embodiment of a laminar hook 370 is shown. The hook 370 can include a pair of legs 372 and a bridge portion 386 pivotably connected to the legs 372 by a hinge joint 384, as shown in FIG. 9A. Each of the legs 372 can include a first end 374 having a screw opening 380 and a second, opposed end 376 including a threaded portion 378 for insertion into a rotatable arm 310, where the leg 372 can be secured to the arm 310 using a fastener 334, similar to the mechanism previously described for laminar hooks 300, 340. The laminar hook 370 of FIGS. 9A and 9B can be similar to laminar hooks 300, 340 in all respects to the manner in which the arms 310 connect to the spacer body 212.

As shown in FIGS. 9A and 9B, the bridge portion 386 can have a substantially U shape, with the free ends 388 terminating at screw openings 390. The midsection 392 of the bridge portion 386 can include a tab 394 extending at an angle therefrom, as illustrated in FIG. 9A. The tab 394 can take any shape and size suitable for gripping or grabbing around the lamina, such as a solid plate as shown. However, it is contemplated that the tab 394 can also be a U-shaped body. Further, the tab 394 can be formed integral to the bridge portion 386 or as a separate component. If desired, the tab 394 may be configured to be angularly adjustable and fixable in a desired angle relative to the bridge portion 386 during implantation for greater flexibility.

In an exemplary method of assembling the laminar hook 370, the bridge portion 386 can be attached to legs 372 by inserting a fastener 382, such as for example, a screw, through openings 380 of the legs and openings 390 of the bridge portion 386. Thereafter, the legs 372 can be inserted into the attached rotatable arms 310 along the sides of the spacer body 212, and secured therein with fasteners 334, such as for example, threaded nuts.

Figure 11B:
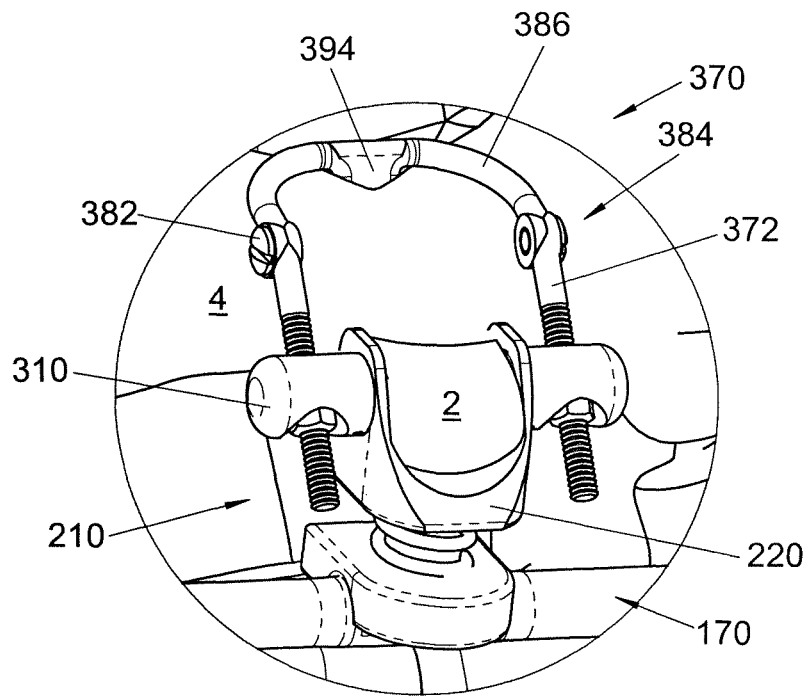
FIG. 11B shows an enlarged view of the implanted device of FIG. 11A.
Figure 11A:
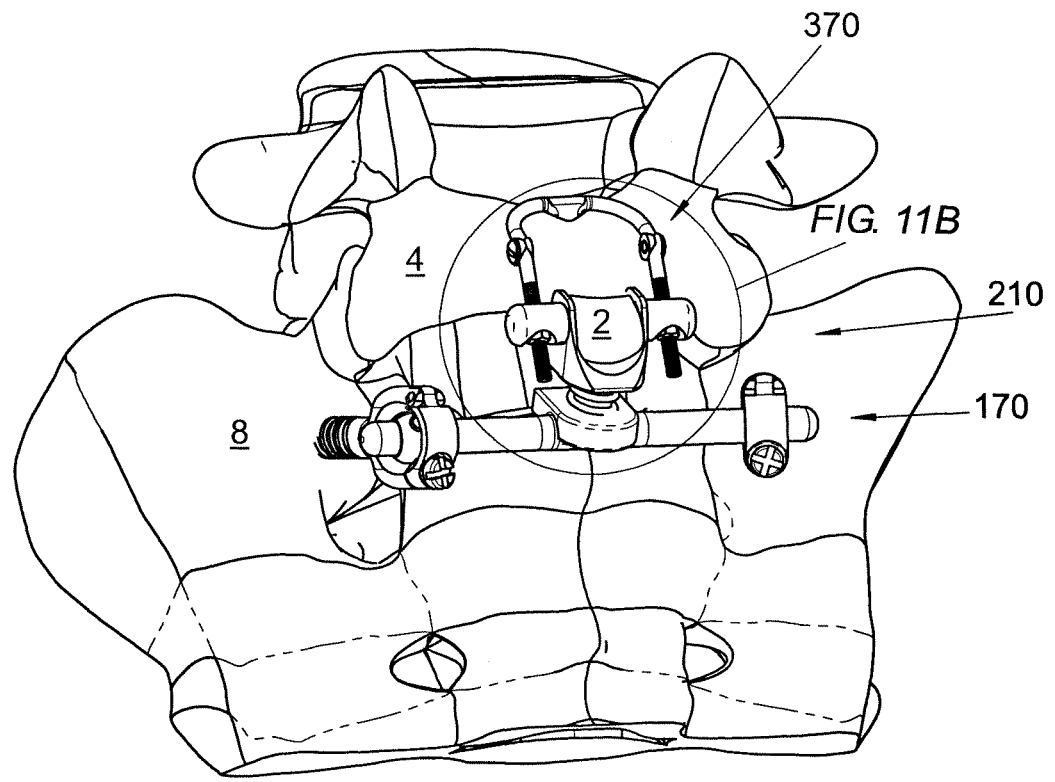
FIG. 11A illustrates a perspective view of the assembled device of FIG. 9A in situ.

As with the previous laminar hooks 300, 340, the fully assembled laminar hook 370 of the present embodiment can assist with the positioning and attachment of the implantable device 210 to the vertebra 4. As illustrated in FIGS. 11A and 11B, the implantable device 210 can be implanted between a vertebra 4 and an adjacent vertebra, such as for example, the sacrum 8. It is understood, of course, that the device 210 may be inserted between any adjacent pair of vertebrae using, for example, a rod and screw system 170 as shown. Once the spinous process 2 of the vertebra 4 is positioned within the saddle region 228 of the spacer body 212, the laminar hook 370 can be clasped onto the lamina with the tab 394 extending around the lamina, as shown in greater detail in FIG. 11B. By providing a hook 370 which is pivotable at two points (i.e., at hinge joint 384 and at rotatable arms 310), the hook 370 can accommodate variations in patient anatomy. Further, it is understood that the legs 372 can be angled or curved so as to better conform to the natural anatomical curves of the lamina, similar to the legs 342 of laminar hook 340.

The implantable device 210 can be implanted with the laminar hook 370 fully attached to the spacer body 212 as described in the methods above. Alternatively, the laminar hook 370 can be fully attached to the spacer body 212 after the implantable device 210 has been inserted between a pair of vertebrae. In this instance, the laminar hook 370 can be partially assembled (i.e., the legs 372 are connected to the bridge portion 386) when the implantable device 210 (including the rotatable arms 310) is implanted. Afterwards, the legs 372 can be secured to the arms 310 with the fasteners 334 once the tab 394 has been properly positioned around the lamina. As previously discussed, the surgeon can adjust the height of the hook 370 by manipulating the fastener 334 with respect to the rotatable arms 310 and legs 372 in order to adapt to variations in the patient's anatomy.

The laminar hooks 300, 340, 370 of the present invention can be formed from a variety of suitable biocompatible materials, either alone or in combination with one another. Suitable materials for forming all or part of the hooks 300, 340, 370 include metals, such as for example, stainless steel, titanium, and their alloys, as well as polymers, such as for example, polyetheretherketone (PEEK). Of course, it is understood that other suitable materials may also be used without departing from the spirit of the present invention.

If desired, it is also possible to provide a unitary fixation body requiring less assembly than the devices previously described for stable support of the spinous process 2, such as the support bodies or brackets 412, 512, 612 provided by the present disclosure. As shown in FIGS. 12A-12C, an implantable device 410 in accordance with one exemplary embodiment of the present disclosure includes a support bracket 412 having similar features to those of implantable device 10. Where applicable, like elements of the device 410 are designated with the same reference numerals as device 10 following the prefix "4". The support bracket 412 can include a bone scaffold portion 420 configured for placement beneath a spinous process 2. The scaffold portion 420 can extend into a neck region 416, which can extend into an anchor portion configured as, for example, a bone plate 480 for attachment to an adjacent vertebra. As shown, the scaffold portion 420 can extend at about a 90° angle with respect to the bone plate 480. However, it is understood that the scaffold portion 420 may extend at various angles with respect to the anchor portion in keeping with the spirit of the disclosure.

Like support body 12, the scaffold portion 420 can include an upper surface 422, a lower surface 424, and a sidewall 426 extending in between. The upper surface 422 can include a contoured area defining a saddle region 428 for placement of the spinous process 2 thereon. Channels 432 may be formed along the sidewall 426 and extend into openings 434 at the upper surface 422, as shown in FIG. 12A. In one exemplary embodiment, one channel 432 may be formed on each lateral side of the scaffold portion 420. Optionally, however, a single channel 432 may be provided which extends across the scaffold portion 420 and opens at both lateral sides. A flexible fixation element 450 such as, for example, a wire, ligament, band, fabric webbing, or suture formed of a metallic, polymeric, synthetic, or natural material, and composites thereof may be passed through the scaffold portion 420 and tied around the spinous process 2, thereby securing the bone to the device 410 as shown in FIGS. 12B and 12C.

The scaffold portion 420 can extend into a bone plate 480, which may include one or more extensions or legs 484. As shown in FIG. 12B, two legs 484 may be provided. Of course, the bone plate 480 may be formed with more than two legs 484 if desired. The legs 484 may further include fastener holes 486 for insertion of fasteners, such as for example, bone screws 488, thereby enabling the secure attachment of the bone plate 480 to a bony surface such as the sacrum 8. In one exemplary embodiment, the legs 484 are positioned so as to flank the median crest when the plate 480 is attached to the sacrum 8. Surface features such as, for example, a bioactive coating and/or teeth 430 may also be provided on the legs 484 for enhancing attachment to the bony surface.

In yet another exemplary embodiment shown in FIGS. 13A-13C, an implantable device 510 including a unitary support body or bracket 512 is shown. The implantable device 510 shares similar features to those of implantable device 10. Where applicable, like elements of the device 510 are designated with the same reference numerals as device 10, following the prefix "5". The support bracket 512 includes a bone carrier portion 520 which extends into a bone plate 580. Like the support body 212 of FIGS. 4 and 5A-5C, the bone carrier portion 520 can include raised sidewalls 526 that form wing-like projections 536. The projections 536 create a deeper saddle region 228 for seating the spinous process 2 therein, and further cradling or supporting the bone during use. Apertures or through-holes 538 may be provided on the projections 536 for attachment of a fixation device. For instance, a flexible fixation element such as those previously described for use with devices 10, 110 may also be applied in this embodiment to secure the spinous process 2 to the carrier portion 520. Alternatively, a rigid fixation element such as a locking cap and bone fastener (not shown) similar to those provided with implantable device 210 may also be utilized to firmly secure the bone to the support bracket 512. Further, a laminar hook 300, 340, 370 similar to the ones previously described may also be implemented with the support bracket 512 of the present embodiment.

Like support bracket 412, the carrier portion 520 can extend into an anchor portion configured as, for example, a bone plate 580 which may include one or more extensions or legs 584. As shown in FIG. 13B, two legs 584 may be provided. Of course, the bone plate 580 may be formed with more than two legs 584 if desired. The legs 584 may further include fastener holes 586 for insertion of fasteners, such as for example, bone screws 588, thereby enabling the secure attachment of the bone plate 580 to a bony surface such as the sacrum 8. In one exemplary embodiment, the legs 584 are positioned so as to flank the median crest when the plate 580 is attached to the sacrum. Surface features such as, for example, a bioactive coating and/or teeth 530 may also be provided on the legs 584 for enhancing attachment to the bony surface.

FIGS. 14A-14C illustrate yet still another exemplary embodiment of the present disclosure. As shown, an implantable device 610 includes a unitary support bracket 612 that comprises a body 616 having a scaffold portion 620 at one end and an anchor portion 680 at an opposite end. The implantable device 610 shares similar features to those of implantable device 10. Where applicable, like elements of the device 610 are designated with the same reference numerals as device 10, following the prefix "6". The scaffold portion 620 may be configured in a similar manner to the scaffold portion 420 of implantable device 410 shown in FIGS. 12A-12C for supporting a spinous process 2. However, in the illustrated embodiment, the scaffold portion 620 extends into a body 616 that terminates at an anchor portion 680. The anchor portion 680 may comprise a pair of legs 684 defining a bone-gripping portion 648 therebetween. In use, the support bracket 612 may be positioned such that the spinous process 2 rests on the saddle region 628 of the scaffold portion 620 and a flexible fixation element 650 secures the bone to the scaffold portion 620. The anchor portion 680 can be positioned to rest against a bony surface of the adjacent vertebra, such as the median crest, where the adjacent vertebra is the sacrum 8. However, it is understood that the implantable device 610 can be modified in size (i.e., height and width) and shape to be used at any level of the spinal column.

The support bodies or brackets 412, 512, 612 of the present disclosure may be provided as rigid fixation devices or as semi-rigid, flexible fixation devices, depending on the materials selected for their construction and the particular needs of the patient. That is, a rigid fixation device may be provided by constructing the brackets from a biocompatible metal, such as for example, titanium or stainless steel, or a rigid polymer, such as for example, polyetheretherketone (PEEK). However, a semi-rigid fixation device having limited flexibility (i.e., compression and/or extension) may be provided by constructing the brackets from a polymer material, such as for example, silicone, a rubber-like material, or a polyethylene such as ultra high molecular weight polyethylene (UHMWPE). Further, it is contemplated that the devices may be constructed from a combination of materials to provide a semi-flexible, semi-rigid fixation device. For example, the brackets 412, 512 may be constructed of mostly metal but for a neck region 416, 516 comprising a polymeric material to enable some compression and/or extension under normal compression loads.

In general, the specific materials included in each portion of the implantable device may be selected based on a desired degree of flexibility and/or compressibility, or to provide biocompatibility and/or bioactive characteristics. A number of biocompatible materials are suitable for forming the devices of the present disclosure. For example, in one embodiment, the device may be formed from a medical grade metal such as pure titanium or a titanium alloy such as titanium-vanadium-aluminum alloy. The device may also be formed from, e.g., stainless steel or cobalt chrome. It is also possible to form the device from a shape-memory material such as nickel titanium or nitinol. Other suitable biocompatible materials include ceramic materials. The ceramic material may be a mixture of particles, for example, a mixture of a metal or metals and/or a ceramic non-metallic material or materials.

The implantable device of the present invention can also be formed from a suitable biocompatible polymeric material. Examples of suitable synthetic polymers include, but are not limited to, polyvinyl alcohol (PVA) and alkylated or acylated derivatives thereof, polyethylene (PE), polyurethane (PU), polypropylene (PP), nylon, polycaprolactone (PCL), and copolymers and combinations thereof. Examples of suitable synthetic non-biodegradable polymers, include, but are not limited to, various polyacrylates, ethylene-vinyl acetates (and other acyl-substituted cellulose acetates), polystyrenes, polyvinyl oxides, polyvinyl fluorides, poly(vinyl imidazoles), chlorosulphonated polyolefins, polyethylene oxides, polytetrafluoroethylenes and nylons. Another polymeric material, which is particularly suitable for use in production of mouldable compositions, is a hydrolysed polymer or copolymer of a vinyl ester, particularly a hydrolysed polymer or copolymer of vinyl acetate. Other preferred polymeric materials include ultra-high molecular-weight polyethylene (UHMWPE) and polyetheretherketone (PEEK).

The flexible portions of the present device, such as the flexible linking member 40 or the compressible cushion 140 in particular, can be formed of a suitable elastomeric material, such as for example, silicone, and natural or synthetic rubber or rubber-like materials. Alternatively, the flexible linking member 40 can be formed of any of the biocompatible metals previously discussed. With regard to the cushion 140 in particular, it is possible to construct the cushion 140 from an elastomeric or viscoelastic material contained within a retaining cover or jacket formed of, for example, a fabric.

A wide variety of fiber materials are suitable for forming the fabric cover, such as for example, polyester, polyethylene, and other high tenacity polymeric fabrics, as well as carbon fiber yarns, ceramic fibers, metallic fibers, including mixtures of one or more of these materials and including fibers made therefrom. The textile fabric may be formed using weaving, knitting, braiding or embroidery. The fabric may be produced in the desired profile or may be reduced to the desired profile from a larger amount of fabric, for instance, by cutting or pressing.

The elastomeric or viscoelastic core material within the fabric cover may comprise any of the suitable materials previously mentioned. The core may also comprise a swellable plastic such as a polymeric composite or hydrogel, such as polyvinylalcohol, polyvinyl pyrrolidone or derivatives of polyacrylic or polymethacrylic acid. Examples of suitable polymers are polyurethanes, polyureas, PAN, polydimethylsiloxanes (silicone rubber), and highly crystalline multiblock acrylic and methacrylic copolymers. Examples of suitable hydrophilic polymers are high-molecular weight polyacrylamide, polyacrylic acid, polyvinylpyrrolidone, polyethyleneoxide, copolymers of ethyleneoxide and propyleneoxide or hyaluronic acid; covalently crosslinked hydrogels such as hydrophilic esters or amides of polyacrylic or polymethacrylic acids; and physically crosslinked hydrogels, such as hydrolyzates or arninolyzates of PAN.

Hydrogels useful for forming the elastomeric material of the flexible cushion 140 include lightly cross-linked biocompatible homopolymers and copolymers of hydrophilic monomers such as 2-hydroxylalkyl acrylates and methacrylates, e.g., 2-hydroxyethyl methacrylate (HEMA); N-vinyl monomers, for example, N-vinyl-2-pyrrolidone (N-VP); ethylenically unsaturated acids, for example, methacrylic acid (MA) and ethylenically unsaturated bases such as 2-(diethylamino) ethyl methacrylate (DEAEMA). The copolymers may further include residues from non-hydrophilic monomers such as alkyl methacrylates, for example, methyl methacrylate (MMA), and the like. Another type of suitable hydrogel includes HYPAN™ and poly(vinyl alcohol) (PVA) hydrogels.

To further enhance the ability of the device to attach to the surrounding bone once implanted, the device may include a number of surface modifications. For example, sections of the implantable device may include surface alterations that may facilitate tissue attachment, bonding or fixation. These alterations may include surface teeth, barbs, beads, surface roughening, or the addition of bioactive coatings to one or more sections of the device. Further, the device may also include roughened or porous surfaces. The roughened or porous surfaces may enhance attachment between implant surfaces and bone tissue. In addition, some porous surfaces may facilitate tissue ingrowth to form a biological bond between sections of the device and the surrounding bone and/or soft tissue. Roughened or porous surfaces may be included on any portion of the device, and in particular, may be desirable for the portions of the device in direct contact with bony tissue such as the upper surfaces 22 of the support bodies 12 or the saddle regions 228 of the support bodies 212 which may benefit from bone tissue ingrowth.

The surface of the device may also include biologically active agents. These agents may include osteogenic factors to further facilitate bonding between components of the device and the surrounding bone and/or soft tissue. Further, the device may include therapeutic agents such as antibiotics, steroids, anti-thrombotic agents, anti-inflammatory drugs, and/or analgesic agents. In one embodiment, the biologically active agent may be contained in a coating on the device. Alternatively, or in addition, the device may be porous and the biologically active agent may be contained in the pores of the device. The biologically active agent may be, for example, bone morphogenic protein (BMP) for inducing cartilage or bone growth.

It is contemplated that the surgeon may use the devices of the present disclosure to treat a number of clinical problems.

For example, the devices may be used to treat degenerative disc disease and/or disc herniation. The devices may also be used to treat spinal stenosis, including central and/or lateral canal stenosis. The devices may be used before, after, or in conjunction with other treatments or implants, including adjacent rigid fixation, adjacent spinal decompression, fusion, and/or facet replacement or repair.

The devices of the present disclosure may be surgically implanted in a variety of ways without impairing the effectiveness of the devices. For example, the surgeon may select a number of different operative approaches and/or incision positions and/or sizes. Further, the surgeon may implant each of the components of the devices in various sequences. The specific operative procedures may be selected based on patient-specific clinical factors.

A number of different incisions and/or operative procedures may be used to implant the devices of the present disclosure. For example, in one embodiment, the surgeon may use a mid-line incision over the lumbar and sacral vertebrae to expose the L5-S1 interspinous region. Alternatively, the surgeon may use one or more incisions positioned lateral to the spine. Further, the surgeon may use a minimally-invasive procedure including various scopes, cannula, and/or robotic implantation devices to deliver the devices to the surgical site.

It is contemplated that the devices 10 of the present disclosure may provide an improved system and method for treating various disorders of the spine. For instance, the devices provide a mechanism for treating disorders of the spine at the L5-S1 vertebral level. Further, the devices of the present disclosure may also be useful for treating diseases of the spine at other vertebral levels. However, the devices of the present invention may also be used to stabilize lumbar vertebrae above the L5 level. For example, in the case of an L5 laminectomy, it is possible to use the present device to stabilize the L4 vertebra while placing the screws of the rod-based device system into the pedicles of the adjacent L5 vertebra, thereby providing a supporting bridge between the L4-L5 region. Accordingly, it is contemplated that the devices provided in this disclosure, and in particular the rod-based systems, may be used to stabilize any pair of adjacent vertebrae by securing the anchors of the rod to the pedicles of the adjacent vertebra to the spinous process being supported.

The methods and devices of the present disclosure may be significantly less invasive and/or produce less drastic and more reversible anatomic changes as compared to other procedures including spinal fusion and total disc replacement. The device of the present disclosure may limit normal spinal motion but provide some controlled movement in flexion, extension, rotation, and/or lateral bending. Further, the devices and methods of the present disclosure may be particularly well-suited for treating various stages of degenerative disc and/or spinal stenosis, particularly at the L5-S1 level.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An implantable interspinous stabilization device, comprising:
   a flexible body including:
      a first portion having a bone-contacting region configured for placement beneath a spinous process of a vertebra;
      a locking cap configured for placement over the spinous process and over the first portion and having slots for receiving a bone fastener while allowing adjustment of a height of the locking cap from the first portion;
      a second, base portion having an attachment end for receiving and holding onto a bone attachment member; and
      a flexible element comprising a spring and connecting the first and second portions; and
      a bone attachment member attachable to the second, base portion to create an adjustable joint with the flexible body, the bone attachment member being configured to secure the device to a bony surface of an adjacent vertebra.

2. The device of claim 1, wherein the first portion comprises a member having a contoured surface defining the bone-contacting region.

3. The device of claim 1, wherein the bone-contacting region comprises a saddle region.

4. The device of claim 3, wherein the saddle region is defined by wing portions.

5. The device of claim 4, further comprising a bone fastener for insertion through the locking cap and wing portions.

6. The device of claim 1, wherein the first portion has a channel for insertion of a flexible fixation element therethrough.

7. The device of claim 1, wherein the bone attachment member comprises a bone plate having a rod-like attachment end for engagement with the second, base portion.

8. The device of claim 7, wherein the second, base portion includes a groove for rotatably receiving the rod-like attachment end of the bone plate.

9. The device of claim 1, wherein the bone attachment member comprises a rod and bone anchor system.

10. The device of claim 9, wherein the second, base portion includes a groove for rotatably receiving the rod.

11. The device of claim 1, further comprising surface modifications for enhanced attachment to bone tissue.

12. The device of claim 11, wherein the surface modifications are selected from the group consisting of teeth, barbs, beads, and surface roughening.

13. The device of claim 1, wherein the device further includes a biologically active material to promote tissue growth after implantation.

14. The device of claim 13, wherein the biologically active material is contained in a coating on the device.

15. The device of claim 13, wherein the device is porous and the biologically active material is contained in the pores of the device.

16. The device of claim 1, wherein the device is comprised of a biocompatible metal or polymer.

17. The device of claim 1, wherein the vertebra is a lumbar vertebra.

18. The device of claim 1, wherein the adjacent vertebra is a sacrum.

* * * * *